(12) United States Patent
Degani

(10) Patent No.: US 7,110,903 B2
(45) Date of Patent: *Sep. 19, 2006

(54) APPARATUS FOR MONITORING A SYSTEM WITH TIME IN SPACE AND METHOD THEREFOR

(75) Inventor: Hadassa Degani, Rehovot (IL)

(73) Assignee: Yeda Research & Development Co., Ltd., Rehovot (IL)

( * ) Notice: Subject to any disclaimer, the term of this patent is extended or adjusted under 35 U.S.C. 154(b) by 420 days.

This patent is subject to a terminal disclaimer.

(21) Appl. No.: 10/342,509

(22) Filed: Jan. 15, 2003

(65) Prior Publication Data

US 2003/0135341 A1    Jul. 17, 2003

Related U.S. Application Data

(60) Division of application No. 09/843,283, filed on Apr. 26, 2001, now Pat. No. 6,553,327, which is a continuation-in-part of application No. 09/101,708, filed as application No. PCT/US97/00801 on Jan. 21, 1997, now Pat. No. 6,353,803.

(51) Int. Cl.
G01F 1/12    (2006.01)

(52) U.S. Cl. ....................... 702/100; 702/104

(58) Field of Classification Search ................ 702/100, 702/104, 23; 600/458, 454; 382/128; 73/38, 73/61.44

See application file for complete search history.

(56) References Cited

U.S. PATENT DOCUMENTS

| | | | | |
|---|---|---|---|---|
| 5,156,152 A | * | 10/1992 | Yamazaki et al. | 600/454 |
| 5,743,266 A | * | 4/1998 | Levene et al. | 600/458 |
| 5,793,883 A | * | 8/1998 | Kim et al. | 382/128 |
| 5,818,960 A | | 10/1998 | Gregory et al. | |
| 5,832,411 A | * | 11/1998 | Schatzmann et al. | 702/23 |
| 6,080,107 A | * | 6/2000 | Poland | 600/458 |
| 6,093,019 A | | 7/2000 | Morandi et al. | |
| 6,155,102 A | * | 12/2000 | Toma et al. | 73/61.44 |
| 6,178,807 B1 | * | 1/2001 | Baldwin et al. | 73/38 |
| 6,315,730 B1 | * | 11/2001 | Hoff et al. | 600/458 |
| 6,353,803 B1 | | 3/2002 | Degani | |
| 2001/0000060 A1 | | 3/2001 | Toma et al. | |

* cited by examiner

*Primary Examiner*—Bryan Bui
*Assistant Examiner*—Xiuqin Sun
(74) *Attorney, Agent, or Firm*—Scully, Scott, Murphy & Presser, P.C.

(57) ABSTRACT

Apparatus and method for monitoring a system in which a fluid flows and which is characterized by a change in the system with time in space. A preselected place in the system is monitored to collect data at two or more time points correlated to a system event. The data is indicative of a system parameter that varies with time as a function of at least two variables related to system wash-in and wash-out behavior. A calibration map is made on a calculated basis with each pixel or voxel representative of a color hue indicative of wash-out behavior and a color intensity indicative of wash-in behavior. When a satisfactory map is obtained, the collected data is processed on the basis of the map to obtain an image of the preselected place with each spatial unit thereof correlated with a color hue and a color intensity. Software and a data processing system are provided to develop the calibration map. The calibration map and image of the preselected place are also novel implementations. Two sets of maps and images can be acquired using different sets of time points.

13 Claims, 23 Drawing Sheets

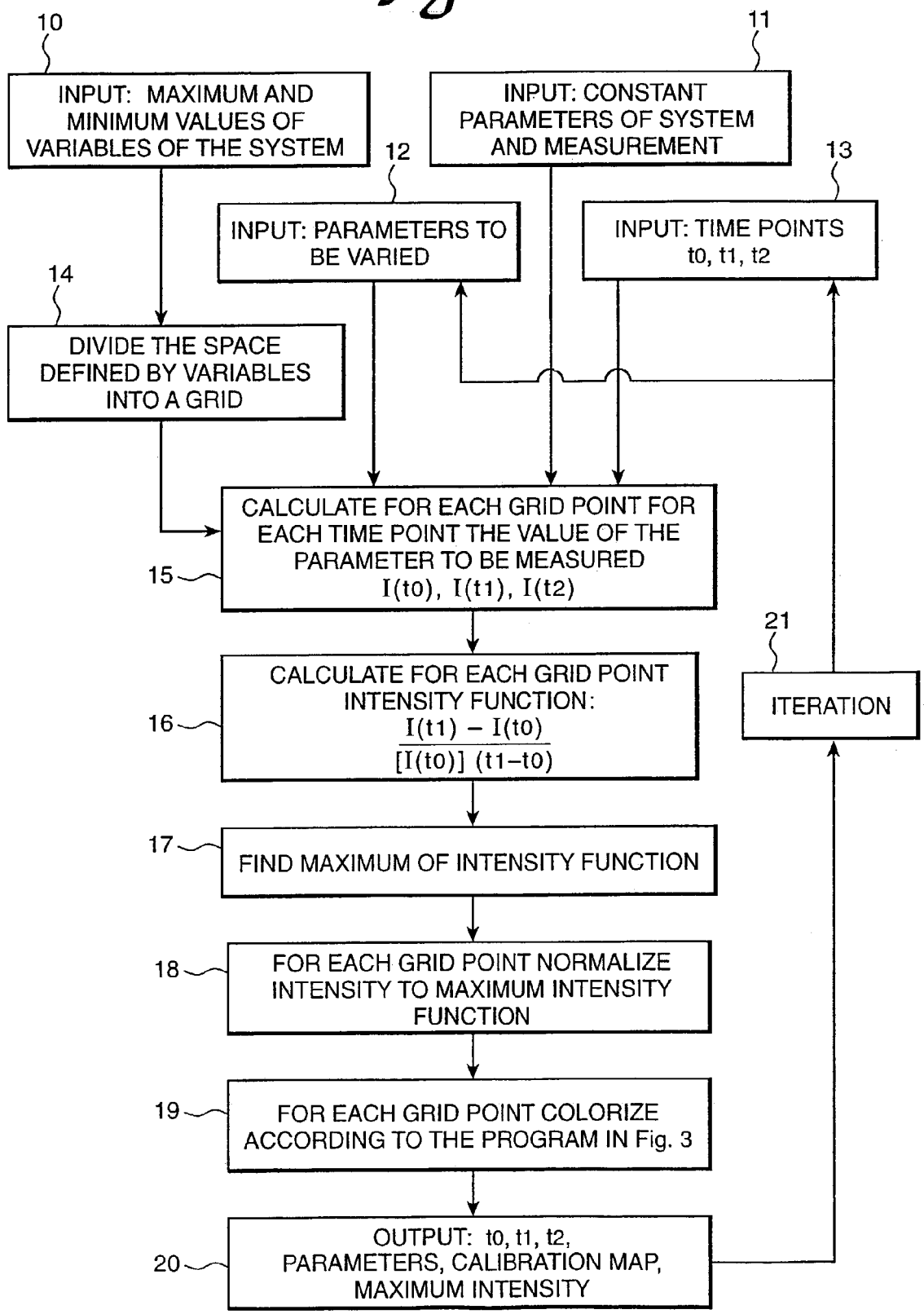

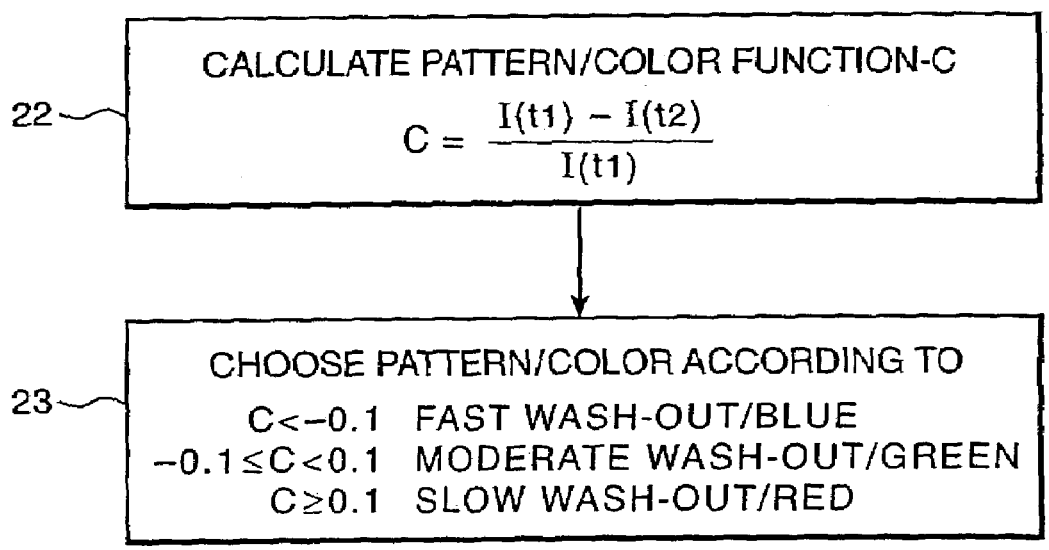

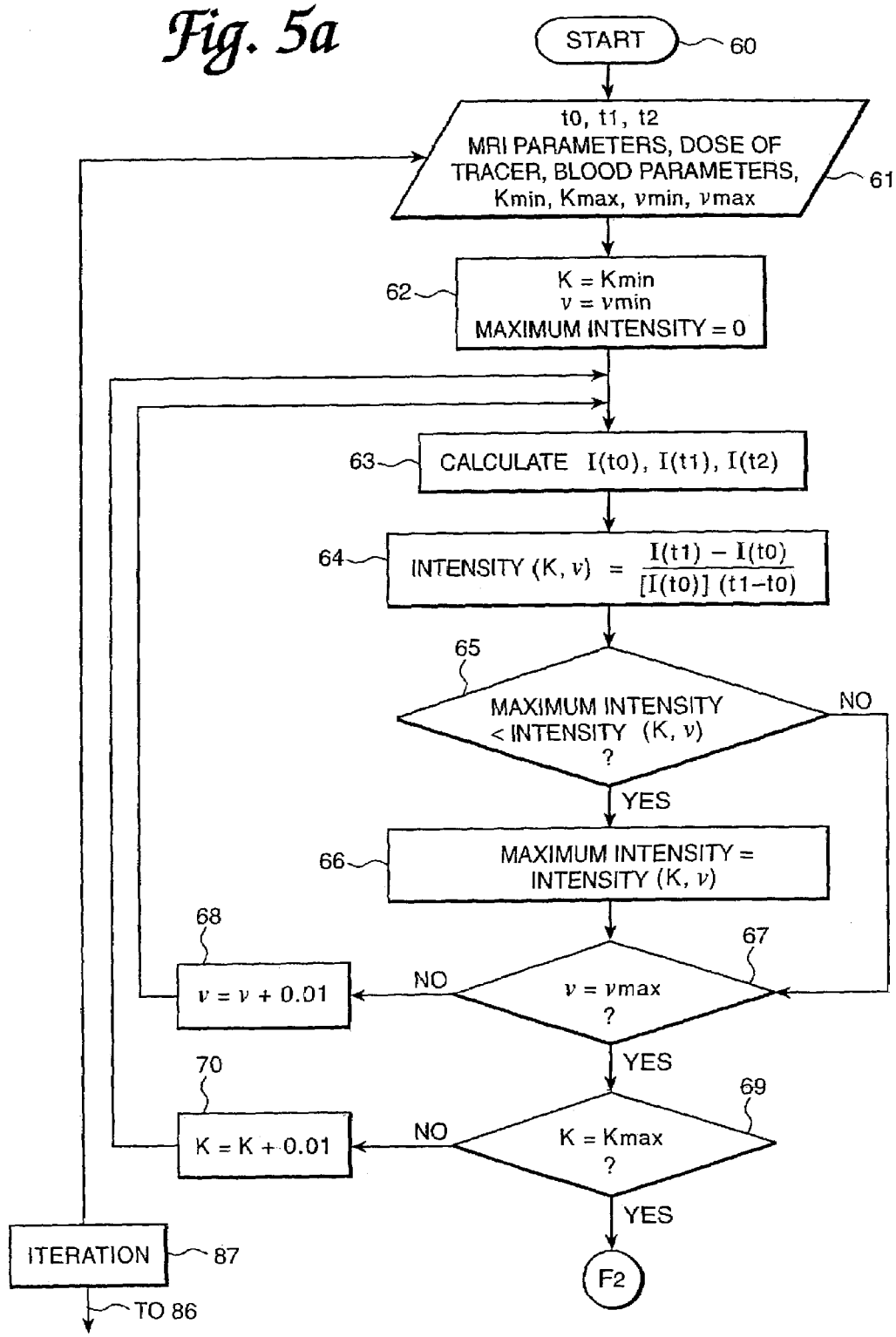

APPARATUS FOR MONITORING A SYSTEM WITH TIME IN SPACE AND METHOD THEREFOR

RELATED APPLICATIONS

This application is a Divisional Application of application Ser. No. 09/843,283, filed Apr. 26, 2001 now U.S. Pat. No. 6,553,327, which is a Continuation-in-Part of application Ser. No. 09/101,708, filed Sep. 16, 1998 now U.S. Pat. No. 6,353,803, which was a National Stage filing of International PCT Application No. PCT/US97/00801 filed Jan. 21, 1997; applicant claims the benefit under 35 USC 120.

BACKGROUND OF THE INVENTION

1. Field of the Invention

The present invention relates to apparatus for monitoring a system with time in space and method therefor and more particularly relates to novel apparatus such as a unique MRI machine, a novel irrigation apparatus for testing the effectiveness of an irrigation system, a novel testing apparatus for determining the efficiency of a heating and/or cooling system, and the like, for testing or controlling a system in which fluid flows and where in the system fluid either dissipates in part or requires regeneration.

2. Description of the Prior Art

Presently apparatuses are known for monitoring testing or measuring a system in which a fluid that is flowing or substances in the fluid will dissipate in part as it traverses the system or will require regeneration. For example, MRI machines are used today to create images with or without administration of a tracer-contrast agent. Customarily, the machine is controlled to take a series of images at discrete time intervals and the images are then dynamically analyzed to obtain an output result. For example, dynamic studies of contrast enhancement in breast tumors have demonstrated that the rate of change in signal intensity is an important parameter for the distinction of breast masses, leading to pharmacokinetic studies. However, it is known that as a result of tumor heterogeneity, there are significant local variations in the time evolution of contrast enhancement, and, therefore, maintaining high spatial resolution in both the recording and analysis steps is very important. In a standard clinical MRI of the breast, it is difficult to achieve high spatial resolution and also maintain high temporal resolution. In most dynamic studies performed previously, the emphasis was on high temporal resolution (at the expense of spatial resolution) monitoring the equilibration in the intravascular space and early diffusion into the extracellular space of the tissue. As a consequence, in standard MRI machines the output results are sometimes inconclusive. The foregoing is also characteristic of other systems in which a fluid flows or a component thereof dissipates in part or requires regeneration, such as, for example, an irrigation system, a heating and cooling system and the like.

SUMMARY OF THE INVENTION

Accordingly, the object of the present invention is to provide an apparatus or a machine, and a correlated method, for monitoring a system, in which a fluid is flowing, with time in space, which will provide more conclusive results regarding system anomalies or system efficiency.

The present invention relates to an apparatus for monitoring a system with time in space. The system can be physical, chemical, biological, physiological, environmental, clinical or any other system in part or in whole, the system evolving with time over space in a certain way. The apparatus of the present invention can function on the basis of one, two, three or higher dimensions. The type and extent of spatial resolution and the number of time points and their spacing, that the apparatus selects, depend on the system and can be varied with a lower limit for the number of time points of two. For example, it can be used for processing time dependent data of radiologic examinations such as MRI, ultra-sonography, X-ray tomography or conventional X-ray, or Nuclear medicine for obtaining diagnosis, prognosis and therapy follow up of tumors or any other pathological disorders. It can be utilized for processing monitoring or controlling environmental data of water irrigation. It can be used to analyze data that will permit determination of leafing areas in pipes. It can be used to analyze data obtained in the food, cosmetic and other industries which involve mixture and solution preparations and determination of their homogeneity. It can be also used to assess the efficiency of heating and/or cooling systems.

There are numerous phenomena that evolve over space with time in a way that can be treated according to the present invention by utilizing a novel approach which is termed herein as by wash-in and wash-out behavior. The wash-in and wash-out are terms that are used symbolically to describe a change in one direction (wash-in) and the reverse change (wash-out) which may not be true reversal but can be any pathway that induces a change. Specifically flow of fluid in a system where the fluid or fluid component dissipates or needs to be regenerated, is described according to the invention as wash-in and washout.

For any wash-in/wash-out situation, it is possible to describe n numbers of patterns of wash-out, when n can range from 1 to any integral number, 2, 3, 4 etc., on the basis of m time points, when m can range from 2 to any integral number of specific time points in the time evolution of the process. The definition of wash-out is not strict and a wash-in can become a wash-out and vice versa.

For each kind of system, the apparatus of the present invention provides means for monitoring, controlling or regulating the system by providing means for setting time points and other optimal parameters of the system. This setting uses a novel calibration map based on a physical model which describes the evolution with time in an approximate or rigorous manner. These calibration maps serve also to interpret quantitatively the final color hue/color intensity coded maps obtained as one of the products of the apparatus.

One particular use of the novel apparatus is for contrast enhanced MRI data in order to obtain products that facilitate specific diagnosis of cancer. The time of start of contrast administration is time point t0 and then two post contrast time points t1 and t2 are utilized. These post contrast times are selected by constructing calibration maps based on modeling the kinetics of contrast enhancement that relates the wash-in/wash-out rates to two pathophysiological parameters: microvascular permeability times surface area (termed in short, microvascular permeability and represented by the letter K) and fraction of extracellular volume represented by v. The calibration map is constructed by the apparatus.

BRIEF DESCRIPTION OF THE DRAWINGS

FIG. 2 is a block diagram of the details of the selecting means of the apparatus in FIG. 1 for setting the parameters for data collection;

FIG. 3 is a block diagram of the details showing the colorize function C of the selecting means of the apparatus of FIG. 1;

FIGS. 5a and 5b are a flow diagram of the selecting means showing the novel apparatus selecting means used as a novel MRI apparatus for collection of MRI images.

FIG. 14 is a graph like FIG. 13 showing the pattern of moderate wash-out/slow wash-in and of moderate wash-out/fast-wash-in;

FIG. 15 is a graph like FIG. 13 showing the pattern of fast wash-out/slow washin and of fast wash-out/fast-wash-in;

(c) 3TP parametric image shows predominantly central bright green and peripheral blue pixels, consistent with a benign lesion (score=2). The 3TP parametric image showed no other suspicious lesions, however due to the multiplicity of similar lesions, the patient is simply being followed. Confirmation of multiple benign lesions will be assumed if no malignancy is diagnosed after two years of mammographic follow-up.

Figure 23A:

FIGS. 23(a), (b) and (c) show, respectively, (a) Optical close-up of mammography (MLO projection) in a 44 yo woman showed a spiculated mass (straight arrow). An unexpected, mammographically occult, 2nd lesion was detected at the location indicated by the curved arrow, as a result of this patient volunteering for the 3TP clinical trial. Pathological diagnosis in both cases was infiltrating ductal cancer.

(b) 3TP parametric sagital plane image of lesion suspected to be malignant by mammography. High predominance of bright red pixels indicates high value of the product of vascular permeability×surface area, and low extravascular volume fraction, indicating high probability of malignancy (score=5).

(c) 3TP parametric image of a second adjacent sagital slice showing a second site very suspicious for malignancy (score 5). The radiologist discussed the scan with the surgeon and both sites were biopsied at the time of surgery confirming unsuspected multifocal malignancy.

DETAILED DESCRIPTION OF PREFERRED EMBODIMENTS

Figure 1:
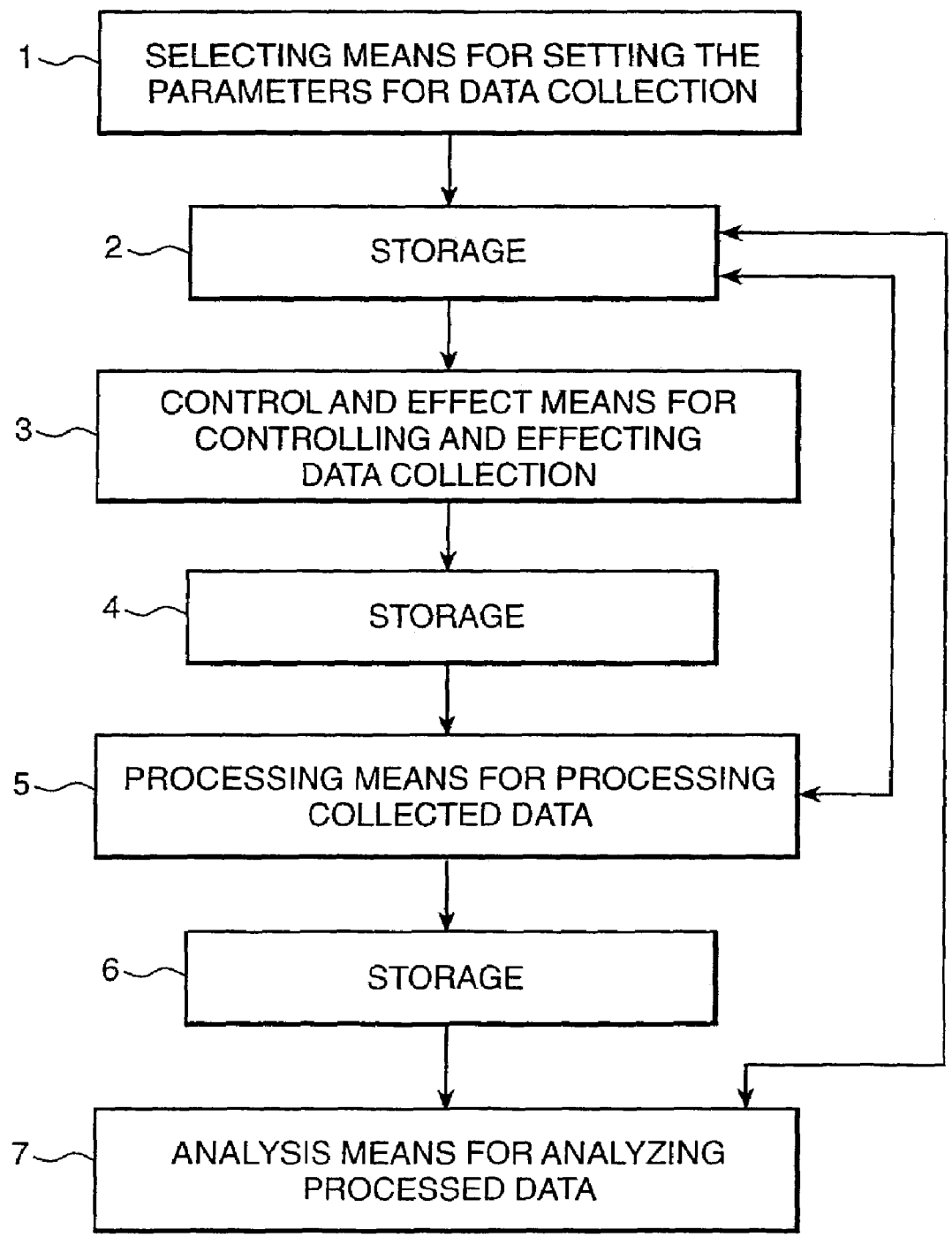
FIG. 1 is a block diagram of the novel apparatus of the present invention for monitoring a system with time in space.

Referring now to FIG. 1, there is shown a block diagram of an apparatus for monitoring a system with time in space which embodies the present invention. This apparatus includes selecting means 1 for setting the time points for data collection, and for setting the parameters of the portions of the apparatus used for data collection, and for processing a colorized calibration map for analysis of processed data that relates variables of the system to unique wash-out/wash-in behaviors which use color hue and color intensity for coding these behaviors. The selecting means is linked to a storage means 2 for storage the selected times, parameters and calibration map. The storage means 2 is linked to a control and effect means 3 for controlling the time and parameters of data collection determined by the selecting means 1 and for effecting the data collection. The means for effecting the data collection 3 are known in the art for which the apparatus will be used.

The control and effect means 3 is linked to a storage means 4 for storing the data collected with time in space. The storage means 4 is linked to a processing means 5 for processing the stored collected data according to a novel unique wash-out/wash-in scheme which uses color hue and color intensity and which is programmed into the processing means 5. The processing means 5 is also linked to storage 2 to receive as part of its input parameters and values set in 1. The processing means 5 is linked to a storage means 6 for storing the processed data. The storage 6 is linked to analysis means 7 for analyzing the processed data. This means 7 is also linked to storage 2 for analyzing the processed data on the basis of the stored calibration map.

All the means can operate sequentially using all storage means, part of the storage means or none. Instead of a storage means, a direct output to input link between blocks 1 to 3 or blocks 3 to 5 or blocks 5 to 7 can exist. The portions of the apparatus need not function all at the same time nor at the same location. Referring now to FIG. 2, there is shown a more detailed block diagram of the selected means, shown in block 1 of FIG. 1. The function of the selecting means is to select time points for data collection, parameters of data collection and for producing a novel calibration map that relates washout/wash-in characteristics coded in color hue/color intensity to variables of the specific system being monitored.

The inputs of the program are blocks 10, 11, 12 and 13 and include the minimum and maximum values for variables of the system being monitored (block 10), input of constant parameters used for data collection (block 11), parameters used for data collection that can be varied (block 12) and three time points selected initially as an intuitive guess from general knowledge of the system as the starting point of an iterative procedure (block 13). The input of block 10 enables the apparatus to divide the system space defined by the variables into a grid, in block 14. For 1 variable, each grid point is a unit length. For 2 variables, each grid point defines a pixel, for 3 variables each grid point defines a volume (voxel). The grid developed in block 14 and the inputs of blocks 11, 12 and 13 serve to determine in block 15, for each grid point, a value for the parameter to be measured at preselected times termed I(t0), I(t1) and I(t2), respectively. This determination or calculation uses an equation specific to the particular system being monitored that can estimate exactly or approximately the change with time in the value of the parameter to be measured for each set of variables of the system. Such equations are well known to those skilled in the art for particular systems. The values of I(t0) and I(t1) calculated in block 15 are used to determine or calculate in block 16, for each grid point, an intensity function according to the equation $$\frac{I(t1) - I(t0)}{[I(t0)](t0 - t1)}.$$

This intensity function represents a wash-in characteristic of initial-rate of wash-in. Then in block 17, by a conventional loop, the grid point with a maximum intensity function is determined and is then outputted to block 18 as maximum intensity. In block 18, all other intensity functions in the remaining grid points are normalized in reference to the maximum intensity. Next, the apparatus in block 19 colorizes each grid point according to the program shown in FIG. 3. Referring to FIG. 3, function C, which determines the pattern of wash-out/color hue, is calculated or determined in blocks 22 and 23 in terms of I(t1) and I(t2), for each grid point, and a wash-out pattern/color hue is chosen according to:

$$C = \frac{I(t1) - I(t2)}{I(t1)}.$$

Figure 13:
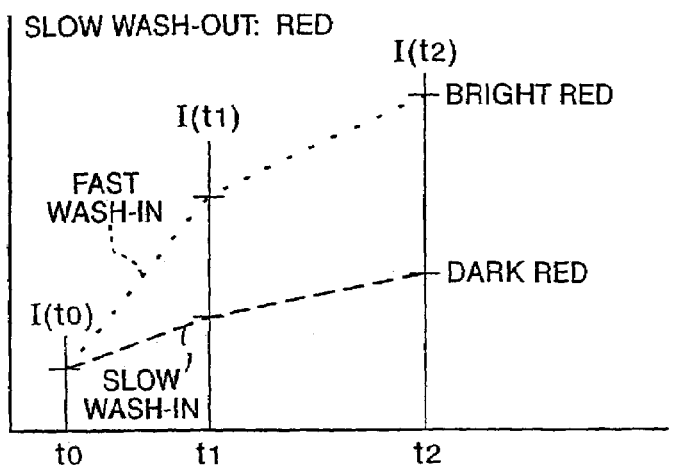
FIG. 13 is a graph showing the pattern of slow wash-out/slow wash-in and slow wash-out/fast wash-in for the three time points t0, t1 and t2 and with data values I(t0), I(t1), I(t2)
Figure 14:
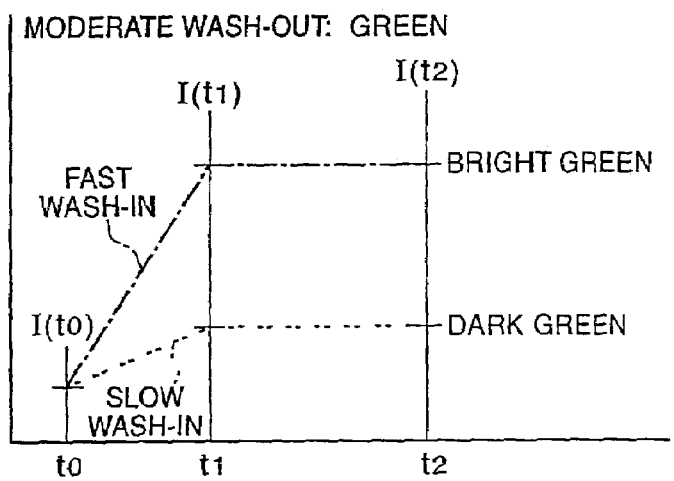
Figure 15:
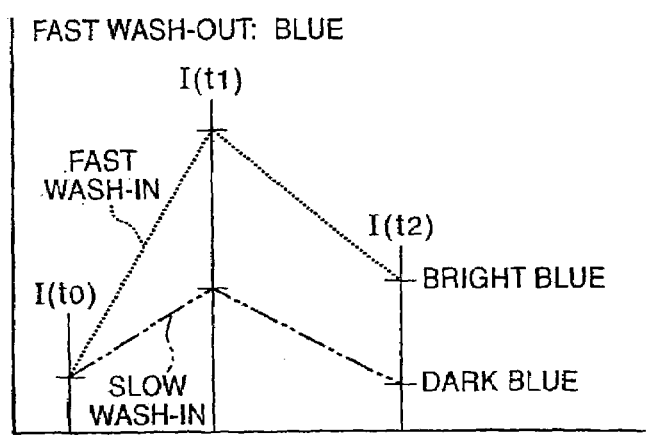

FIGS. 13, 14 and 15 describe systematically the principles of choosing a wash-out pattern which is coded in color hue and of choosing wash in initial rate (apparent initial rate) coded in color intensity. The first pattern (FIG. 13) is the slow wash-out pattern defined by I(t1)<I(t2) and is determined by $$\frac{I(t2) - I(t1)}{I(t1)} \geq 0.1.$$

This pattern is for example coded with the color red. If the $$\text{intensity function} = \frac{I(t1) - I(t0)}{[I(t0)](t1 - t0)},$$

which is a measure of the apparent initial rate of wash-in, has a high value for a slow wash-out pattern, than the red color will be bright reflecting fast wash-in (FIG. 13). If the intensity function has a low value for a slow wash-out pattern than the red color will be dark reflecting slow wash-in (FIG. 13).

The second pattern is the moderate wash-out pattern (FIG. 14) defined by I(t1)≈I(t2) is determined by $$-0.1 < \frac{I(t2) - I(t1)}{I(t1)} < 0.1.$$

This pattern is, for example, coded with the color green. As in the red case, if the intensity function has a high value for this moderate pattern, then the green color will be bright (FIG. 14). If, however, the intensity function has a low value, the green color will be dark (FIG. 14). The third pattern (FIG. 15) is the fast washout pattern defined by I(t1)>I(t2) and is determined by $$\frac{I(t2) - I(t1)}{I(ti)} \leq 0.1.$$

This pattern is coded for example blue. Again if the intensity function is high, namely, wash-in apparent initial rate fast, the color blue will be bright (FIG. 15). If, however, the intensity function is low, the color blue will be dark (FIG. 15). Thus, for each pattern of wash-out coded by a color hue, there can be defined a wash-in rate which relates to the intensity function which determines color intensity. The separation between different wash-in rates depends on the range of color intensities chosen. Referring again to FIG. 2, in block 20 the apparatus, in the final output for the selected t0, t1 and t2 and for the selected system parameters, assigns to each grid point that defines values of the variables of the system a color hue and a color intensity. The colorized and intensity normalized grid points collectively are termed a "calibration map". If the composite calibration map for the selected t0, t1, t2 and for the selected system parameters is satisfactory as will be explained in detail hereafter, the program ends and sends the output to storage in block 2 (FIG. 1) or directly to block 3 (FIG. 1). If the calibration map is not satisfactory, the apparatus makes an appropriate adjustment of the three time points, for example, by incrementing t1 and t2 and inputs into block 13. Alternatively, the apparatus can increment new values for parameters of the system and/or of the measurement, as preselected, and input into block 12. Also, both time points and these parameters can be changed. The steps in the program are repeated using the original inputs of blocks 10 and 11 and going from blocks 14 to 20. This iteration (block 21 in FIG. 2) can be repeated until a satisfactory calibration map is obtained for a set of preselected times and parameters.

In the definition of the intensity function in block 16 (FIG. 2) and the definition of the pattern of wash-out/color hue function C in blocks 22 and 23 (FIG. 3) it is assumed that I(tI)>I(t0). In cases where I(tI) is negative but the absolute value of /I(t1)/ is higher than I(t0) the definitions hold for the absolute values. The choices for coloring function C in block 23 (FIG. 3) are not limited to the specific examples of C<−0.1, −0.1<_C<0.1 and C>_0.1, but any other fraction (such as 0.05 or 0.2) can be used to define C depending on the system.

Figure 4A:
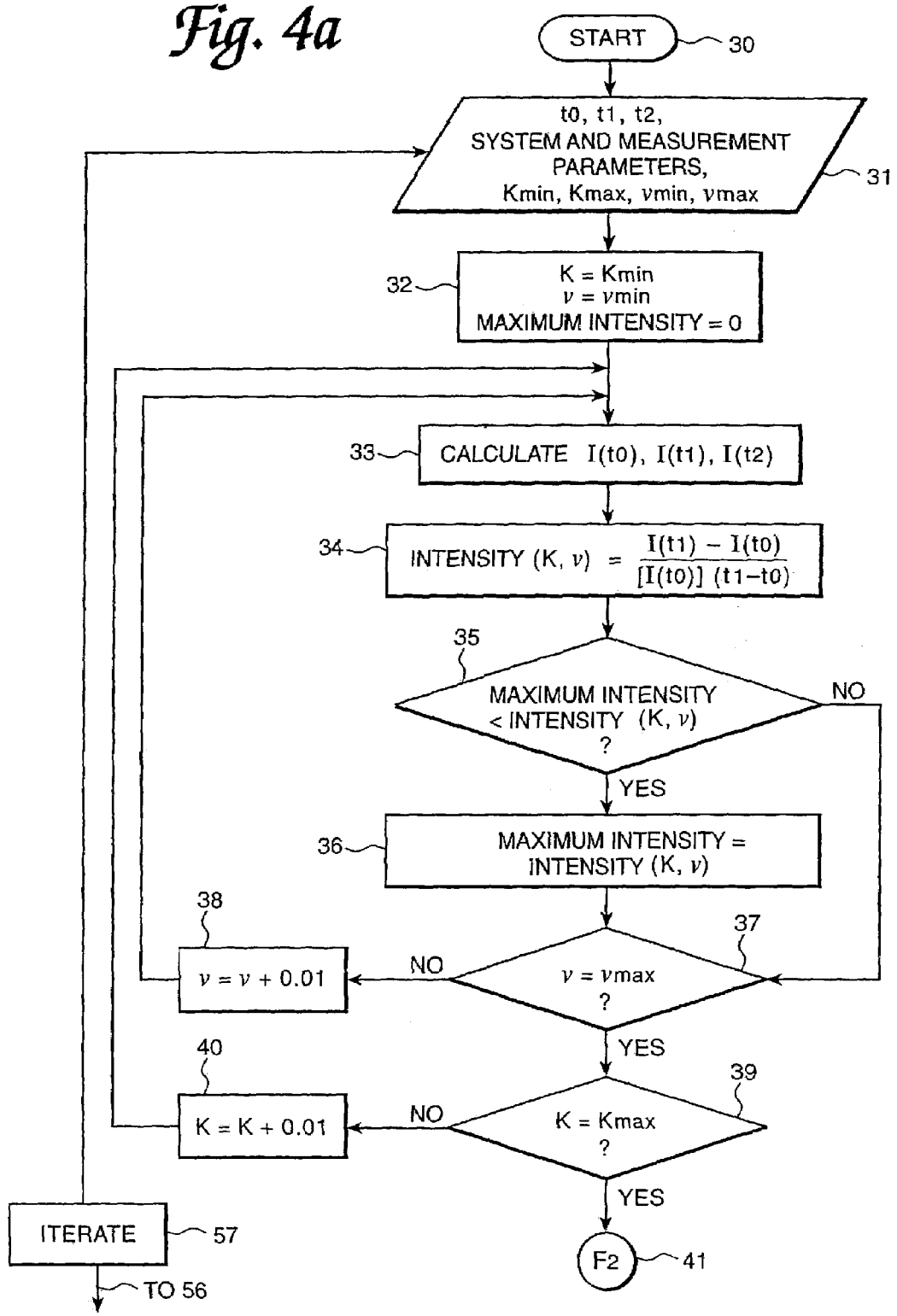
FIGS. 4a and 4b are a flow diagram of the selecting means of the apparatus of FIG. 1 illustrating the setting of the parameters for data collection.
Figure 4B:
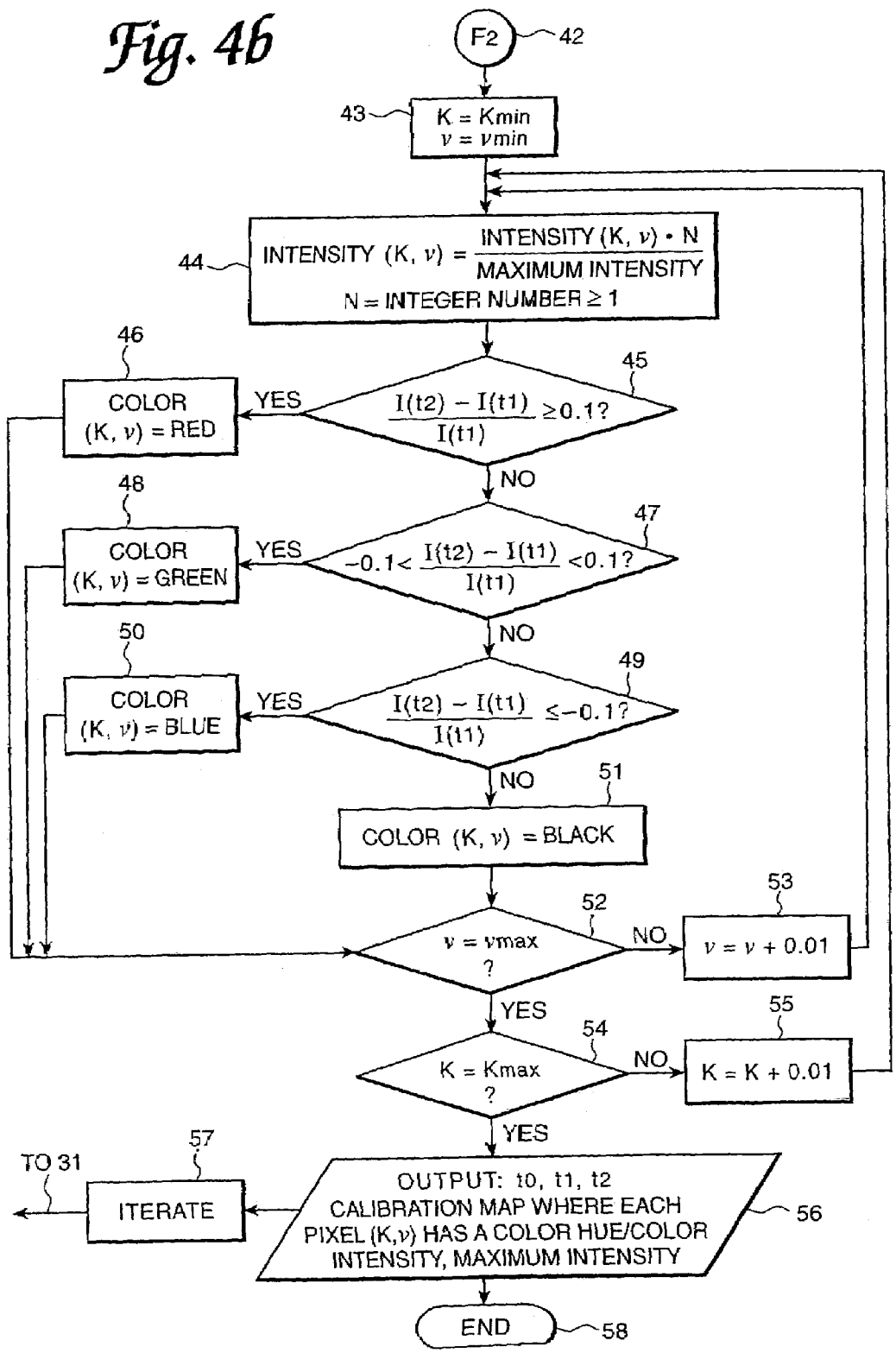

Referring now to FIG. 4, there is shown a flow diagram (steps or blocks) for setting the parameters for data collection and creating a calibration map. This flow diagram is written for a monitored parameter that varies with time as a function of two variables of the system assigned here with the letters K and v. For each grid point in a 2 dimensional grid of K and v, a pixel of dimension of 0.01 units of K and 0.01 units of v is defined in steps or blocks 38, 40, 53 and 55. The program starts in block 30 and gets inputs of the time points, t0, t1 and t2, system and measurement parameters and the range of K and the range of v between their min. and max. values in block 31. The program starts from pixel (K min, v min) in block 32 to calculate I(t0), I(t1), I(t2) in block 33 using an approximate or exact equation correlated to the system being monitored, as is known, that estimates how the parameter monitored with time I(t) depends on K and v, and on other system parameters. The determined or calculated I(t1) and I(t0) are used to calculate for each pixel Intensity (K, v) as shown in block 34, which represent wash-in initial rate. The program is then searching whether the pixel has max. Intensity (blocks 35 to 40) and proceeds through all the pixels in a loop mode returning to block 33 and going again through the steps 34 to block 40 until it reaches the pixel with maximum K and maximum v. Through this loop, the pixel with max. intensity is identified and intensity is calculated for all pixels (K, v). Now, the program proceeds to calculate for each pixel starting from pixel (K min, v min) block 43 a normalized intensity, block 44 normalized relative to the max. intensity. The pixel with max. intensity is assigned with a maximum value for intensity N. N can be 1, 2, 3 or any number such as, 8, 64, 256 (computer numbers), etc. depending on the demands of the system. Then, the program calculates the wash-out pattern for each pixel starting from pixel (K min, v min) until it reaches pixel (K max, v max) and codes with color hue each pattern as shown in blocks 45 to 54. Now, all pixels have a color hue and a normalized color intensity. This produces in the output a calibration map of K, v in block 56 for the selected t0, t1, t2 and system and measurement parameters. If the calibration map is not satisfactory e.g. excessively slanted toward one color hue, new time points, or new system or measurement parameter values, or all are adjusted in the direction to correct the calibration map and bring it to a more satisfactory balance from a color distribution standpoint. The program goes through all the steps in the flow diagram again using the new inputs until a satisfactory calibration map is obtained, which sets the selected time points and system parameters. What will be a satisfactory calibration map depends on the system and will be apparent to one skilled in the art. For most systems a satisfactory map will have about a third of the pixels red, a third green and a third blue.

Figure 5B:
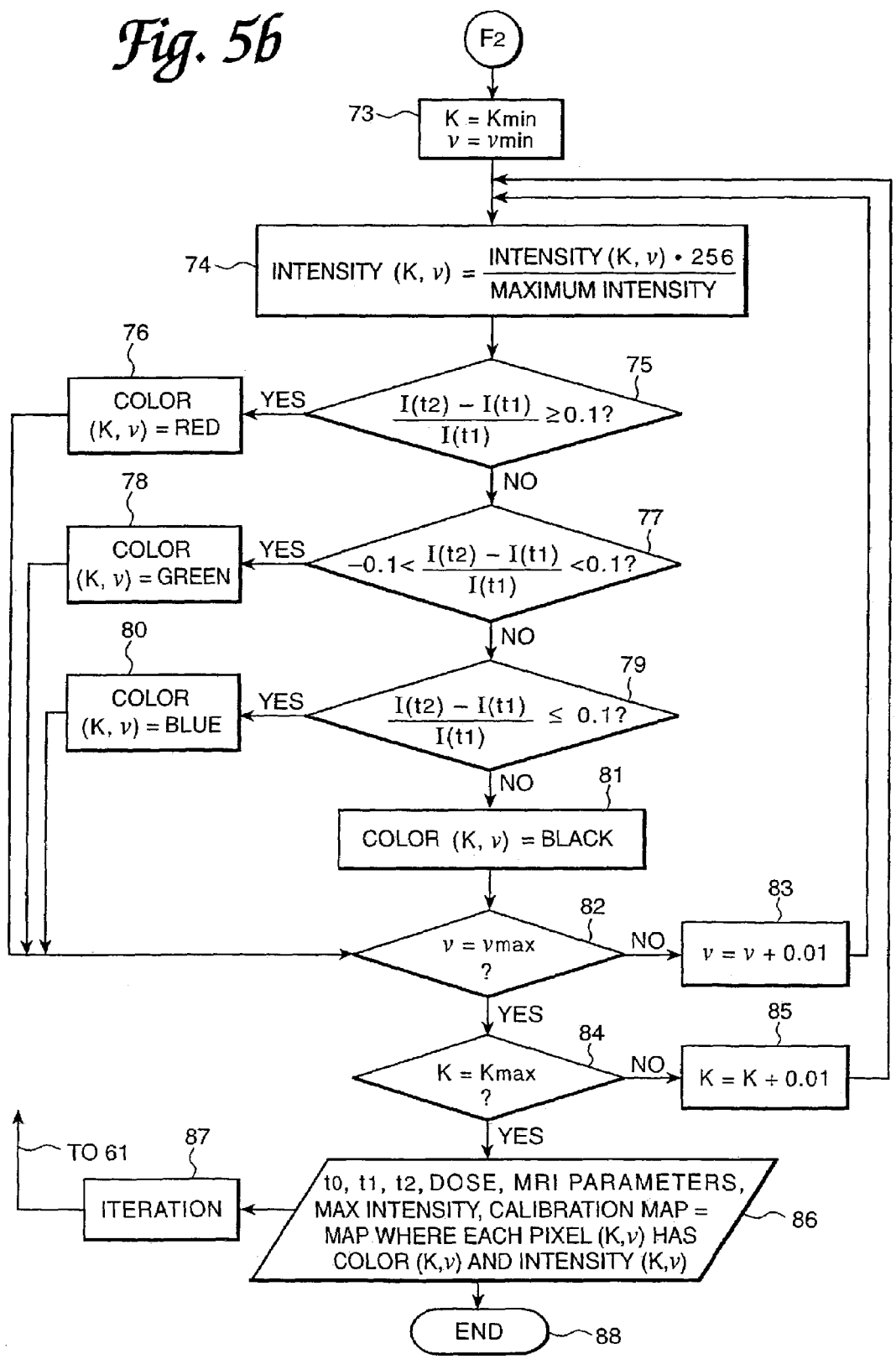

A specific example of a flow diagram for setting the parameters for tracer modulated NM, termed also contrast enhanced MRI, is shown in FIG. 5. The MRI signal is the monitored parameter that is changing with time as a result of administrating a tracer, termed also contrast agent. The input parameter in step 6 includes the three time points t0, t1 t2. These time points are obtained initially by experience in step 87 and are subjected to an iterative process until the best three time points are obtained. Other inputs are the tracer-dose and the MRI parameters that define how the NM signal is recorded. Both the tracer dose and MRI parameters can be constant, or can be optimized by the iterative process in step 87. The input also includes pharmacokinetics parameters that define the tracer change with time in the blood, and max. and min. values for the two variables K and v that define pathophysiological characteristics of the system, namely, a subject body. The variable K defines microvascular permeability which estimates the capacity of blood vessels to leak out the tracer. The variable v defines the fraction of extracellular volume which estimates the amount of free space in a tissue. The steps 62 to 85 in this flow diagram follow the steps 32–54 in FIG. 4. In this flow diagram the maximum intensity is assigned in step 74 to have the value of 256. The output in step 86 consists of a calibration map of the two variables K and v ranging between K min, v min to K max, v max for a specific set of time points and the other inputs. Each pixel in this map with specific K, v values has a color hue and a color intensity. A satisfactory calibration map is defined by reaching a certain distribution of the colors or of the colors and color intensities. For example, a satisfactory map can be a map that divides the K-v plan or plane, or volume between the three colors to The output in step 86 consists of a calibration map of the two variables K and v ranging between K min, v min to K max, v max for a specific set of time points and the other inputs. Each pixel in this map with specific K, v values has a color hue and a color intensity. A satisfactory calibration map is defined by reaching a certain distribution of the colors or of the colors and color intensities. For example, a satisfactory map can be a map that divides the K-v plan or plane, or volume between the three colors to approximately three equal areas, namely, approximately a third of the pixels in the calibration map are red, a third are green and a third are blue.

Figure 16:
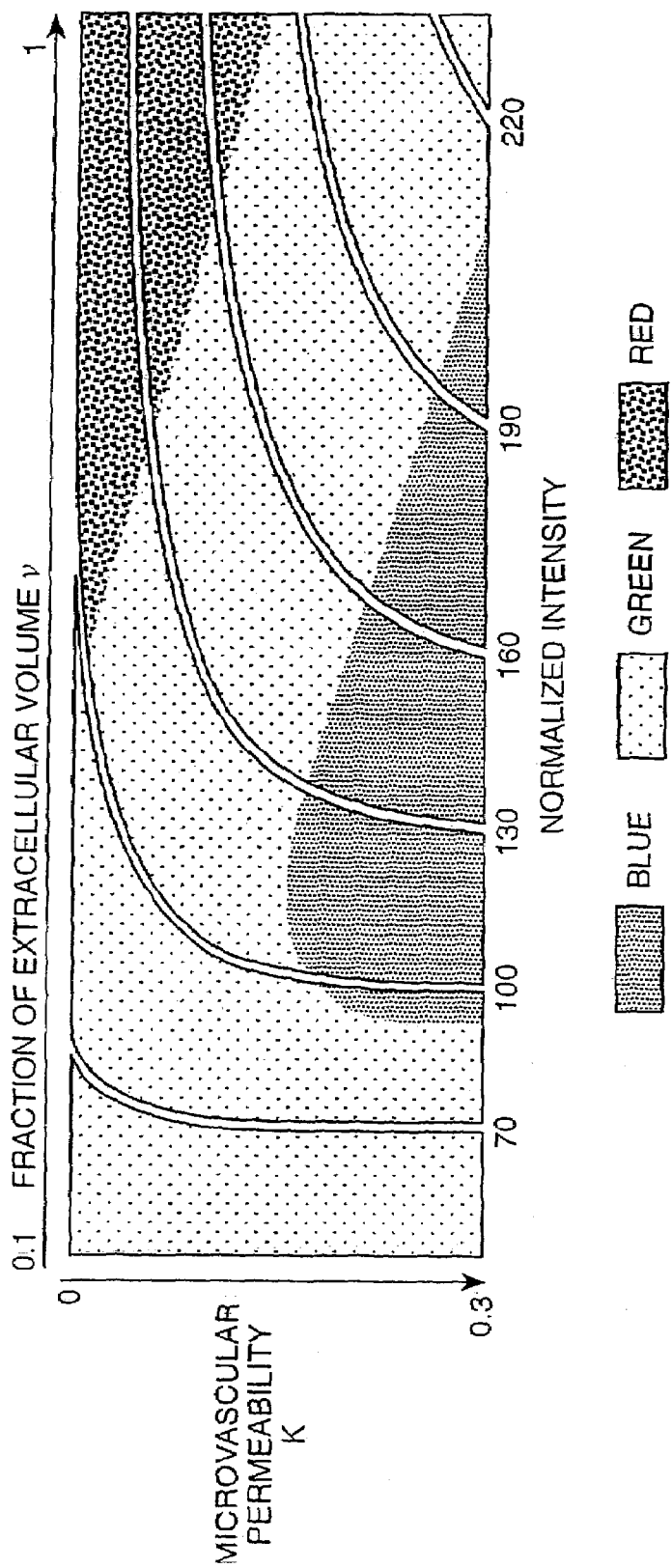
FIG. 16 is a schematic illustration of a typical calibration map as used in the novel apparatus for MRI.
Figure 17A:
FIGS. 17(a), (b) and (c) show, respectively,
 (a) MLO mammographic projection of a 49 yo woman does not show 15 mm cancer which was palpable and diagnosed by in-office FNA as infiltrating ductal cancer.
 (b) Subtraction sagital MRI (0 minute (pre-contrast) image subtracted from 2 minute image shows ring-enhancing, spiculated malignancy in the anterior breast (arrow). Posteriorly, a small intramammary lymph note also enhances, but has a characteristic morphology, including fatty hilus (arrowhead).
 (c) 3TP parametric similar to that of 1b, but overlay of colored pixels is superimposed on MRI image by 3TP software based on a physiological model (described in text). Bright red indicates high probability for malignancy and this lesion was prospectively given a score of 5 (highly suspicious for malignancy).
 (d) Calibration map corresponding to patient shown in 1a. Color hue (red, green, blue) is based on differences in signal intensity between the second and third images of the three image 3TP image set. Color intensity is based on the difference in SI between the first and second images of the image set. As described in the text, areas of high vessel permeability×surface area and low extravascular volume fraction (EVF), typical of malignancy, will be coded as bright red. For optimal discrimination of benign and malignant lesions, the imaging parameters are chosen to approximately divide the calibration map into equal areas of red, green and blue.
Figure 17B:
Figure 17C:
Figure 17D:
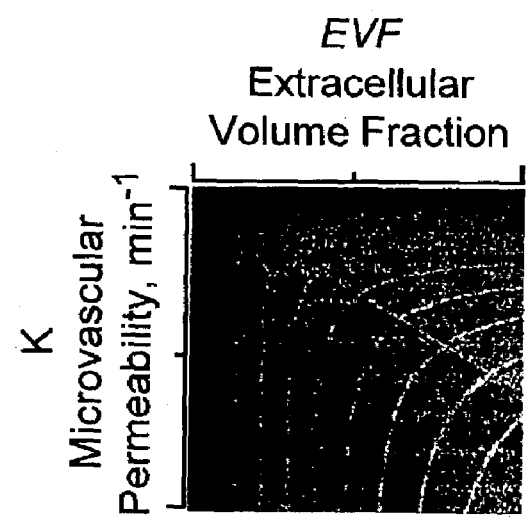

Shown in FIG. 16 is a typical calibration map according to the present invention. The map was created based on the equations of contrast enhancement as known in the art, for the variables microvascular permeability K and fraction of extracellular volume v. The map is constructed as an expected pattern (e.g., color and color intensity) for any three or more selected time points. More explicitly, and with reference to FIG. 16, a three-dimensional representation in a two-dimensional drawing is used. FIG. 16 shows the time points for humans using a gradient echo and a tracer dose of 0.08 mmol/kg, with the time points: t0=0, t1=4 and t2=12 min. These time points were selected in order to discriminate between e.g., fibroadenoma and carcinoma. The isotherms represent regions of the same intensity in each pattern, e.g., same initial rate of wash-in. One dimension is microvascular permeability K ranging between values of interest (for example, 0.00 min$^{-1}$ to 0.3 min$^{-1}$. The second dimension is fraction of extracellular volume v ranging between 0.1 to 1 and the third dimension, normalized intensity is actually the intensity of each color (for example, any value between 0 to 256 intensities). This calibration map serves to determine optimal preset time points t0, t1 and t2 and other parameters such as dose. For different systems it is possible to select different optimal time points. The calibration map also serves to interpret the output of the processing means of the apparatus, which for the specific example of MRI is a 3TP image, defined subsequently in the description. It is clear that if the three time points are chosen to be very close together the calibration map will show only a slow wash-out behavior, namely, the red pattern according to the above example will predominate. On the other hand, if the last point is chosen very far in time, the calibration map will be dominated by fast wash-out, namely, dominated by blue. The suitable 3 time points for a specific system are selected by having all three colors distributed in the most revealing way, namely, in the calibration map about one third of the area is occupied by each color.

Flow Diagrams similar to the flow diagram in FIG. 5 exist for other specific systems. At the final output, a satisfactory calibration map of the variables for an optimal set of t0, t1, t2 and other inputs is always obtained.

Figure 6:
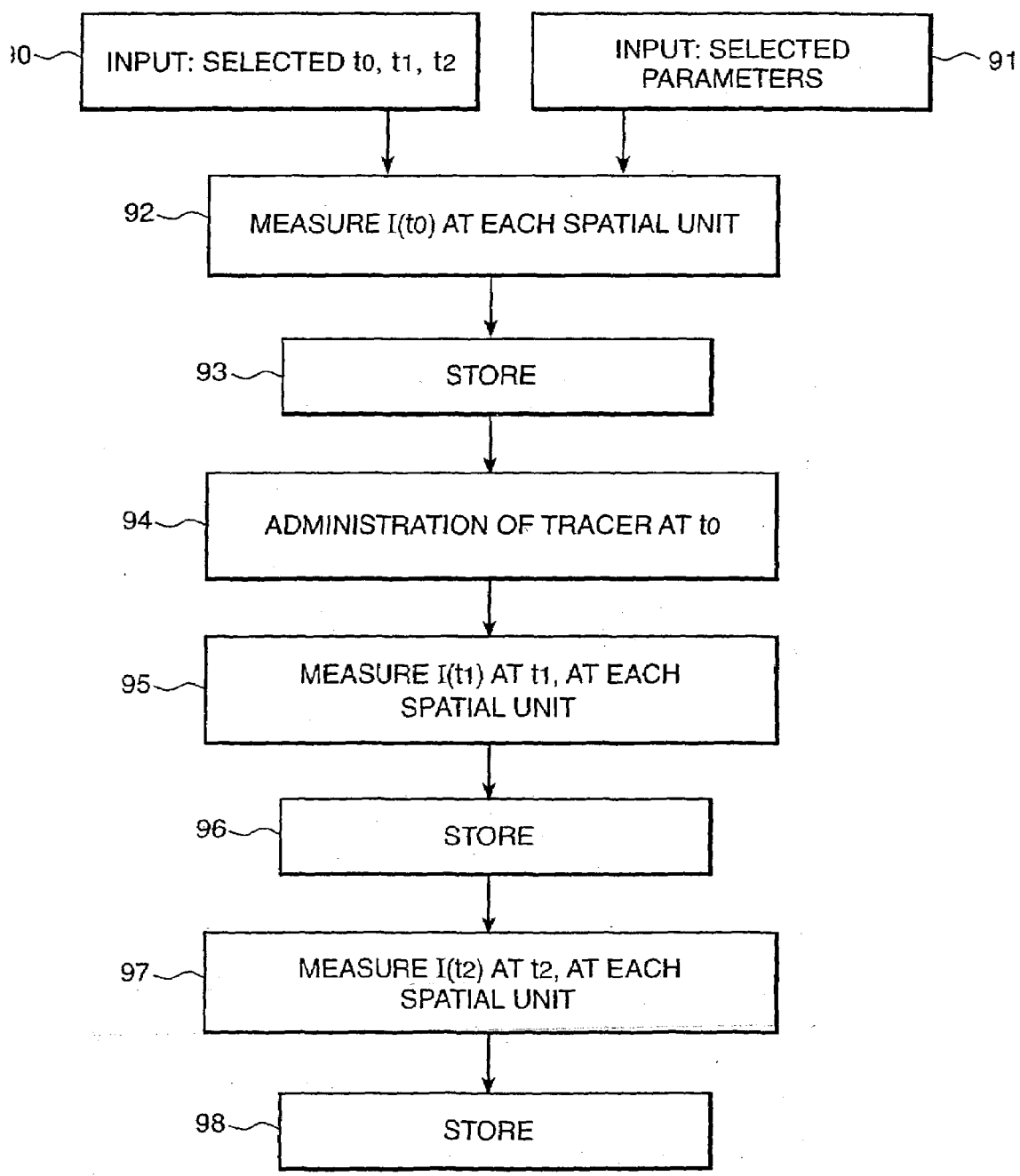
FIG. 6 is a block diagram of the apparatus of FIG. 1 showing in detail the control and effect means of the apparatus for controlling and effecting data collection on a system.

The time points and parameters are set at block 1 (FIG. 1) and are used by the control and effect means 3 to control and effect the data collection (FIG. 1). Referring now to FIG. 6, there is shown a detailed block diagram for controlling and effecting data collection. The input in blocks 90, 91 can be directly obtained from the storage 2 (FIG. 1) or from block 1 (FIG. 1). The measurements in blocks 92, 95 and 97, are performed by means specific for each system. Such means are known in each art. There must be control of times of tracer administration and of measure so that t0, t1 and t2 of the input are accurately controlled. The injection or administration of tracer in block 94 into the system can be performed in any known way. The timing of the tracer administration is fixed to start at t0 and should end usually, but not necessarily before t1, preferably close to t0. The data collected in blocks 92, 95 and 97 are transferred to processing means 5 (FIG. 1) either directly from block 3 (FIG. 1) or from storage 4 (FIG. 1).

Figure 7:
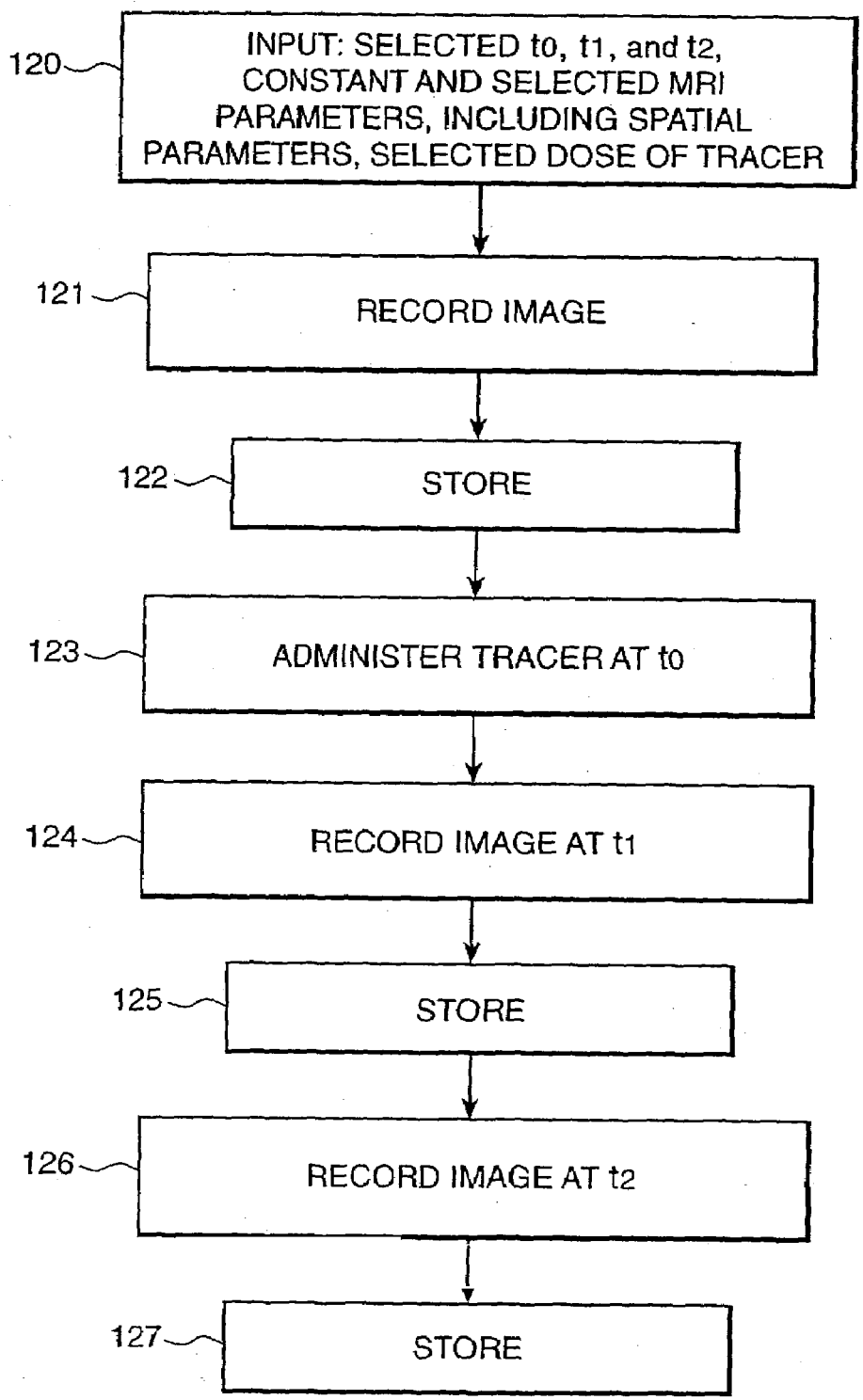
FIG. 7 is a block diagram of the apparatus as applied to MRI and shows the details of the control and effect means of the apparatus for controlling and effecting MRI data collection on a subject.

A specific example of a block diagram of a control and effect means for controlling and effecting the data collection, as part of a modified MRI. apparatus or machine for tracer modulated MRI, is shown in FIG. 7. The control and effect means shown in the block diagram of FIG. 7 receives as an input in block 120 the time points t0, t1 and t2 set by the selecting means in block 1 in FIG. 1, and described in detail for this specific example in the flow diagram 1 of FIG. 4. The other inputs relate to the MRI parameters and to the dose of the tracer and the pharmacokinetic parameters of the tracer that is injected into the blood of the subject. The MRI parameters and the dose of tracer are set by the selecting means in block 1 of FIG. 1, and are described in detail for tracer modulated MRI in the flow diagram of FIG. 4. Next, the apparatus, in block 121 in FIG. 7 records an image of a defined area or a defined volume in the system, namely a body, by means known in this art. The recording parameters are those set by the selecting means 1 in FIG. 1 and inputted into block 12 FIG. 7. The image is then stored in block 122 and a tracer, termed also a contrast agent, is administered at time t0 into the body in block 123 by any known way. This administration is timed to start at t0 for a duration that ends preferably, but not necessarily, close to time point t0 and before recording at time t1. After the administration of tracer, the apparatus, in block 124, at time t1 records an image of the same area or volume as was recorded in block 121 in the same body using the same NM parameters as in block 121. This image is stored in block 125. Next, at time t2, the apparatus, records another image of the same area or volume in the same body, using the same NIRI parameters as in block 121, and then stores this image in the storage of block 127.

Figure 8:
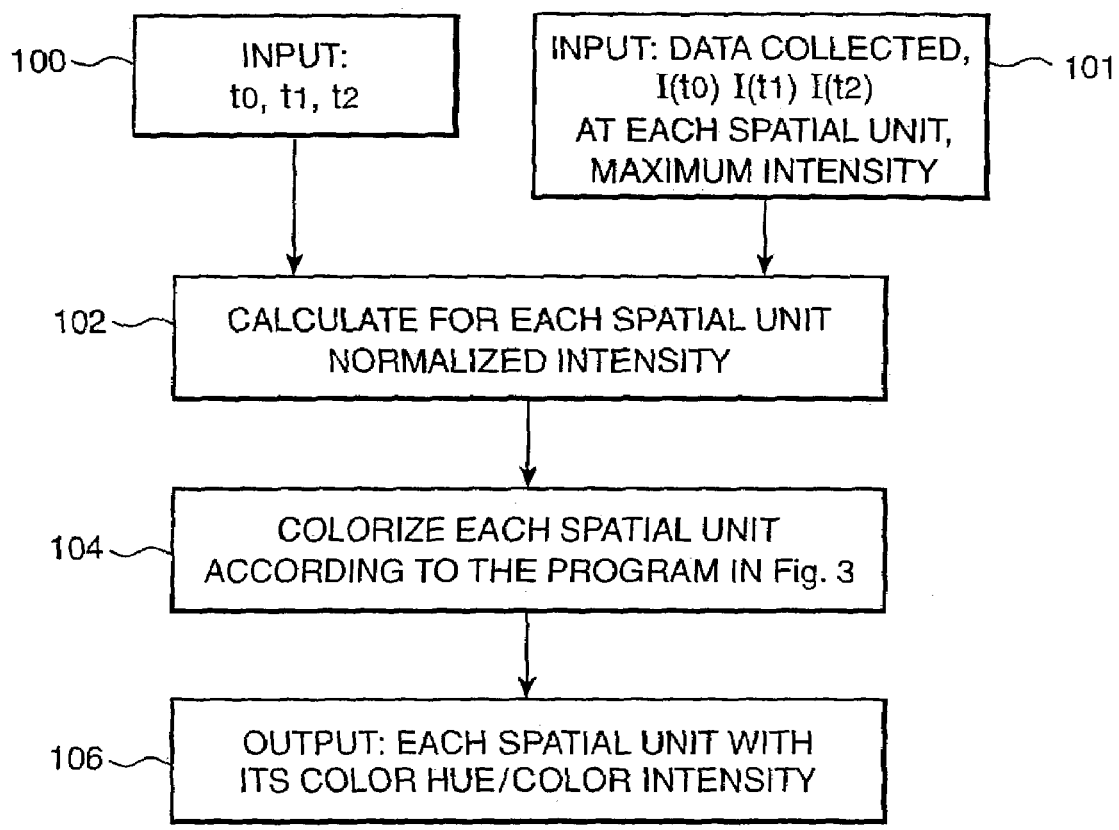
FIG. 8 is a block diagram of the apparatus of FIG. 1 showing details of the processing means of the apparatus for processing the collected data.

Referring now to FIG. 8 there is shown a more detailed block diagram of processing means shown in block 5 of FIG. 1. The inputs shown in block 100 of FIG. 8 are the time points t0, t1 and t2 set in block 1 of FIG. 1 and used in block 3 of FIG. 1. Another input shown in block 101 of FIG. 8 includes the data collected in block 3 of FIG. 1. These data can be directly transferred from block 3 of FIG. 1 or from the storage in block 4 in FIG. 1. The data in block 101 of FIG. 8 for each spatial unit are presented by three data values obtained at three different times. The first data value for each spatial unit, is termed I(t0) and is obtained before administration of the tracer. The tracer and/or third is administered at time point t0. Thus, the first data value is measured before time point t0 but as close to this time point as possible. The second data value for each spatial unit is obtained at time point t1 and is termed I(t1). The third data value for each spatial unit is obtained at time point t2 and is termed I(t2). Another input in block 101 in FIG. 8 is max Intensity. The max Intensity value is part of the output of the selected means as shown in block 20 in FIG. 2.

From the data I(t0), I(t1) and the time points t0, t1 the normalized intensity is then determined in block 102 for each spatial unit. The normalized intensity is given by the equation $$\frac{[I(t1) - I(t0)] \times N}{[I(t0)](t1 - t0) \times (\text{Max Intensity})}.$$

I(t0), I(t1) and Max Intensity have been inputted in block 101. N is an integer number that can be 1,2,3 or 8, 64, 256 (computer numbers). N in block 102 in FIG. 8 is equal to N in block 44 in FIG. 4, in the same monitoring of a system. Next, the apparatus in block 104 colorizes each spatial unit according to the program shown in FIG. 3. The final output in block 106 will have each spatial unit assigned with a color hue and a color intensity. The color hue represents a wash-out pattern and the color intensity represents an initial rate of wash-in. The colored output in block 106 is fed to storage 6 in FIG. 1 or directly to the analysis means in block 7 of FIG. 1. For each color and color intensity in each spatial unit in the output in block 106 of FIG. 8 there is the same color and color intensity in at least one grid point or location in the calibration map with defined values of variables of the system. Thus, the color/color intensity in each spatial unit obtained by the processing means 5 can be related to defined values of variables determined in the calibration map.

Figure 9:
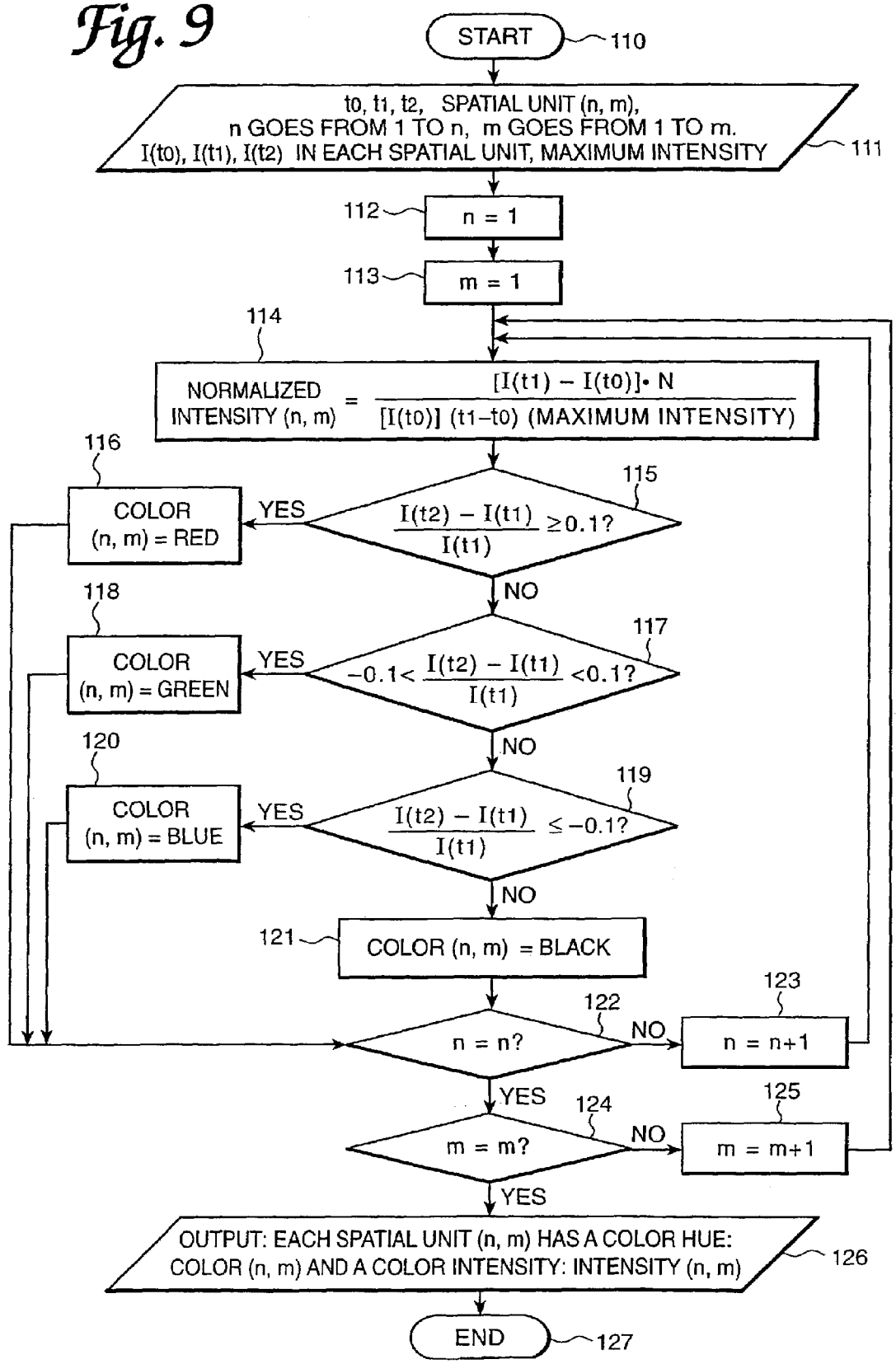
FIG. 9 is a flow diagram of the apparatus of FIG. 1 showing details of the processing means of the apparatus for processing data collected in two dimensions.

The apparatus shown in FIG. 1 functions with normalized intensities. The normalization is performed by selecting means in block 1 in FIG. 1 in the process of obtaining a calibration map defined in detail previously. The selecting means defines max intensity and uses the value of this max intensity to normalize all intensities measured to this max intensity. Alternatively, it is possible, but not preferred, to separate the normalization in reference to max intensity, performed by the selecting means, from that performed by the processing means, by choosing the maximum intensity independently by the selecting means and by the processing means. However, this weakens the correlation between the calibration map and the final output of data processing shown in block 106 of FIG. 8 and in block 126 of FIG. 9 and in block 166 of FIG. 10. Referring now to FIG. 9, there is shown a flow diagram of steps or blocks of the apparatus for processing collected data. This diagram deals with data recorded in two dimensions so that each data point is a pixel. The first step 110 in FIG. 9 is the start. This is followed by input in step 111. The input consists of the selected time points t0, t1 and t2 set by the selected means in block 1 in FIG. 1 and used by the control and effect means in block 3 in FIG. 1. The spatial units n and m define. a pixel in a grid. For the first pixel n=1 and m=1 and then n goes from 1 to n and m goes from 1 to m in steps of 1. Another input is the collected data I(t0), I(t1) and I(t2) of each pixel. This input can be directly obtained from the control and effect means in block 3 in FIG. 1 or from the storage in block 4 of FIG. 1. The input also includes the max intensity which is obtained in the output of the selecting means shown in block 20 in FIG. 2 or in step 56 in the flow diagram of FIG. 4. Next, the apparatus, in steps 112 and 113 in FIG. 9 selects the first pixel n=m=1 and in step 114 determines the normalized intensity in this pixel defined by the intensity function $$\frac{I(t1) - I(t0)}{[I(t0)](t1 - t0)}$$

and by the normalization in reference to the max intensity of $$\frac{N}{\text{Max Intensity}}$$

where N=integer≧1 as defined above. The normalized intensity is a measure of the initial rate for the wash-in behavior. N in step 114 is equal to N in step 44 in FIG. 4 in the same monitoring of a system. Next, this pixel (n=m=1) is colorized in steps 115 to 120 using the color function C according to the block diagram in FIG. 3 and according to steps 45 to 50 in FIG. 4. This determines wash-out pattern/color hue of this pixel. If none of the possible patterns (3 patterns) occur, for example, as 1(t1)=0 this pixel is colored in black in step 121. In steps 122, 123, 124, 125 the next pixel is selected and a loop to step 114 that follows until step 120 determines for this next pixel the normalized intensity and the pattern/color hue. This loop is repeated for all pixels (n×m). In the output of step 126 in FIG. 9 each pixel has a wash-out pattern coded by a color and a wash-in initial rate coded by color intensity. The output is followed by step 127 which ends the flow diagram of FIG. 9.

Figure 10:
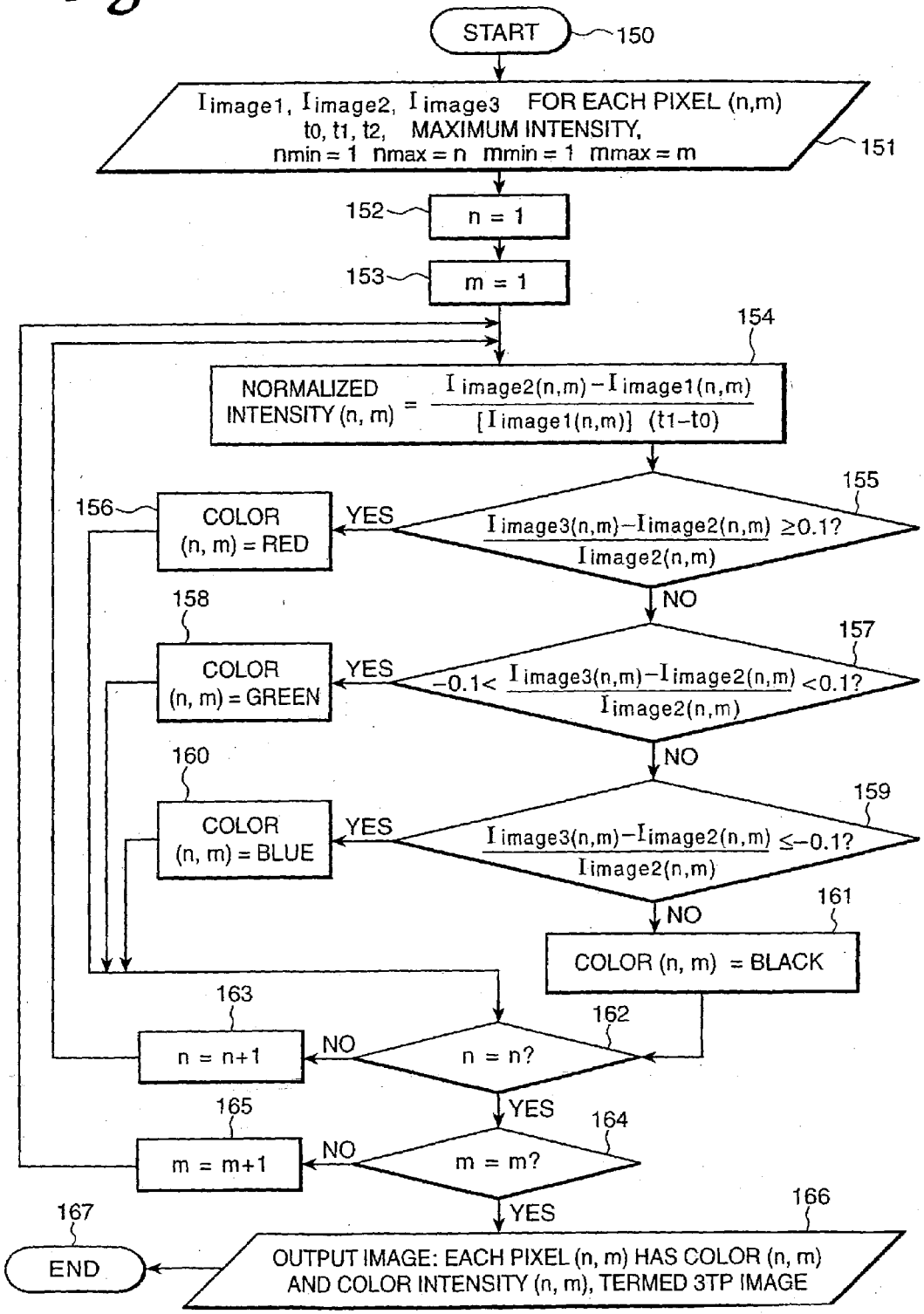
FIG. 10 is a flow diagram of the apparatus of FIG. 1 showing the details of the processing means used for MRI for processing images collected from a subject.

A specific example of a flow diagram of apparatus for processing data collected for tracer modulated MRI is shown in FIG. 10. The flow diagram starts with step 150. The next, step 151, is the input of the selected time points t0, t1, t2 set by the selecting means of the apparatus as shown for tracer modulated MRI in the apparatus depicted in the flow diagram of FIG. 5 and is part of the output step 86 in FIG. 5. These three time points are also used by the control and effect means for data collection in the same monitoring of the body in step 151 of FIG. 10. Maximum intensity is also obtained from the output step 86 in FIG. 4 and is obtained in the same monitoring of the system, namely, the body. The input also includes the data collected by the control and effect means as shown for tracer modulated MRI in FIG. 7. These data are recorded images. There are three recorded images or three sets of recorded images of the same area or volume. The first image or set of images is recorded prior to tracer administration. The second image or set of images is recorded at time t1 and the third image or set of images is recorded at time t2. Each pixel or voxel in the image has an MRI signal intensity which is changing with time after tracer administration. In the first image recorded prior to tracer administration, but close to the administration time, the intensity is termed $I_{image1(n,m)}$. The pixel for which n=1 and m=1 is called the first pixel with intensity $I_{image1(1,1)}$. There are n×m pixels where n goes from 1 to n and m goes from 1 to m. The intensity in each pixel (n,m) in the second image recorded at time point t1 is termed $I_{image2(n,m)}$. Similarly the intensity in each pixel (n,m) of the third image recorded at time point t2 is termed $I_{image3(n,m)}$. In steps 152 and 153 in FIG. 10 the pixels are assigned starting from n=1 and m=1. In step 154 in FIG. 10 the normalized color intensity is determined for pixel (n,m) from the values of pixel (n,m) in $I_{image1(n,m)}$ and $I_{image2(n,m)}$ according to:

$$\text{normalized intensity} = \frac{I_{image2(n,m)} - I_{image1(n,m)}}{[I_{image1(n,m)}](t_1 - t_0)} \times \frac{256}{\text{max intensity}}$$

The normalized intensities are determined for all pixels by a loop in steps 162, 163, 164 and 165 until all pixels have been processed.

Next, in steps 155 to 160 the wash-out pattern/color is determined for each pixel (n,m) from the values $I_{image2(n,m)}$ and $I_{image3(n,m)}$ using the color function C which is defined for this specific example as:

$$C = \text{Color Function} = \frac{I_{image2(n,m)} - I_{image3(n,m)}}{I_{image2(n,m)}}$$

and a color is chosen as shown in block 23 in FIG. 3, and as shown in steps 155 to 159 in FIG. 10. Pixels that are left uncolored through 155–160 as is the case when $I_{image2(n,m)}$=0 are assigned black in step 161. The colorizing steps are looped by steps 162, 163, 164, 165 to include all pixels. The output in step 166 shows an n×m image in which each pixel (n,m) has a defined wash-out pattern/color hue and a defined wash-in rate/color intensity. This colored image is termed the three time points image or, in short, 3TP image. The color hue and color intensity is correlated to the calibration map and interpreted in terms of the values of microvascular permeability K and fraction of extracellular volume v, the two variables of the subject body in the calibration map of the output in step 86 in FIG. 5.

Figure 11:
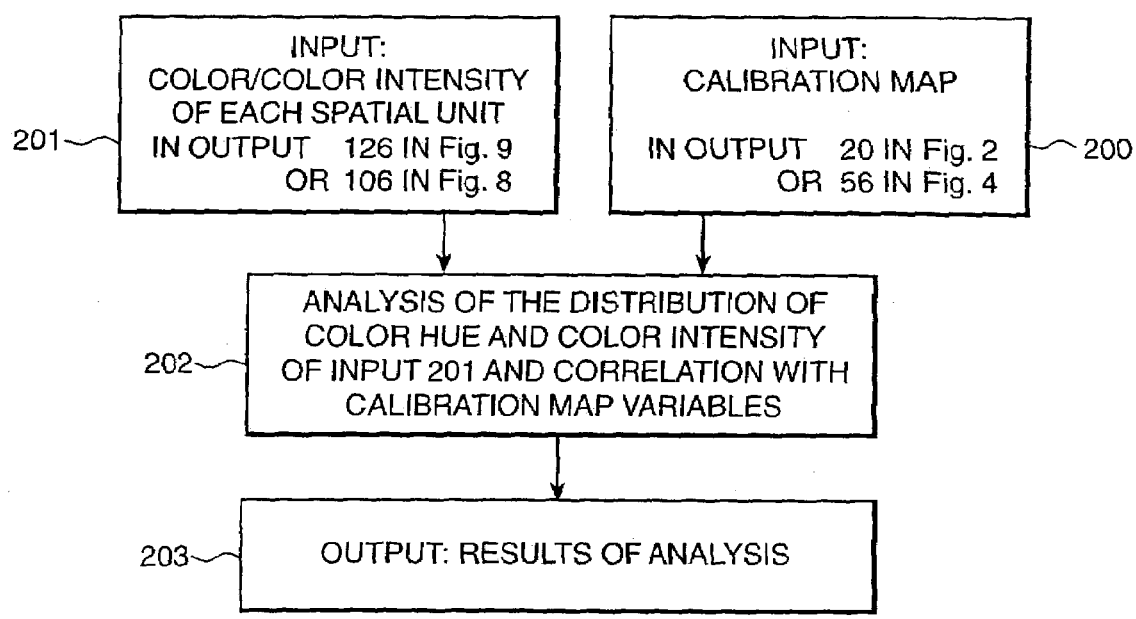
FIG. 11 is a block diagram of the apparatus of FIG. 1 showing the details of the analysis means of the apparatus for analyzing the processed data.

Referring now to FIG. 11, there is shown a block diagram of the structure of the analysis means 7 of FIG. 1. The input in block 200 consists of the calibration map obtained by the selecting means 1 and included in the output in block 20 in FIG. 2 or in the output in block 56 in FIG. 4. The other input in block 201 of FIG. 11 is the output of the processing means shown in block 126 in FIG. 9 or in block 106 in FIG. 8. The input in block 200 and the input in block 201 are from the same monitoring of the subject system. The analysis in block 202 consists of analysis of distribution of colors and of color intensities using for example histograms. The analysis consists also of a correlation between the calibration map and the color/color intensity of each spatial unit of the input in block 201. This correlation estimates values of the variables of the calibration map for each spatial unit in the input of block 201. Finally, the apparatus in block 203 outputs the distribution analysis and the correlation with the calibration map.

Figure 12:
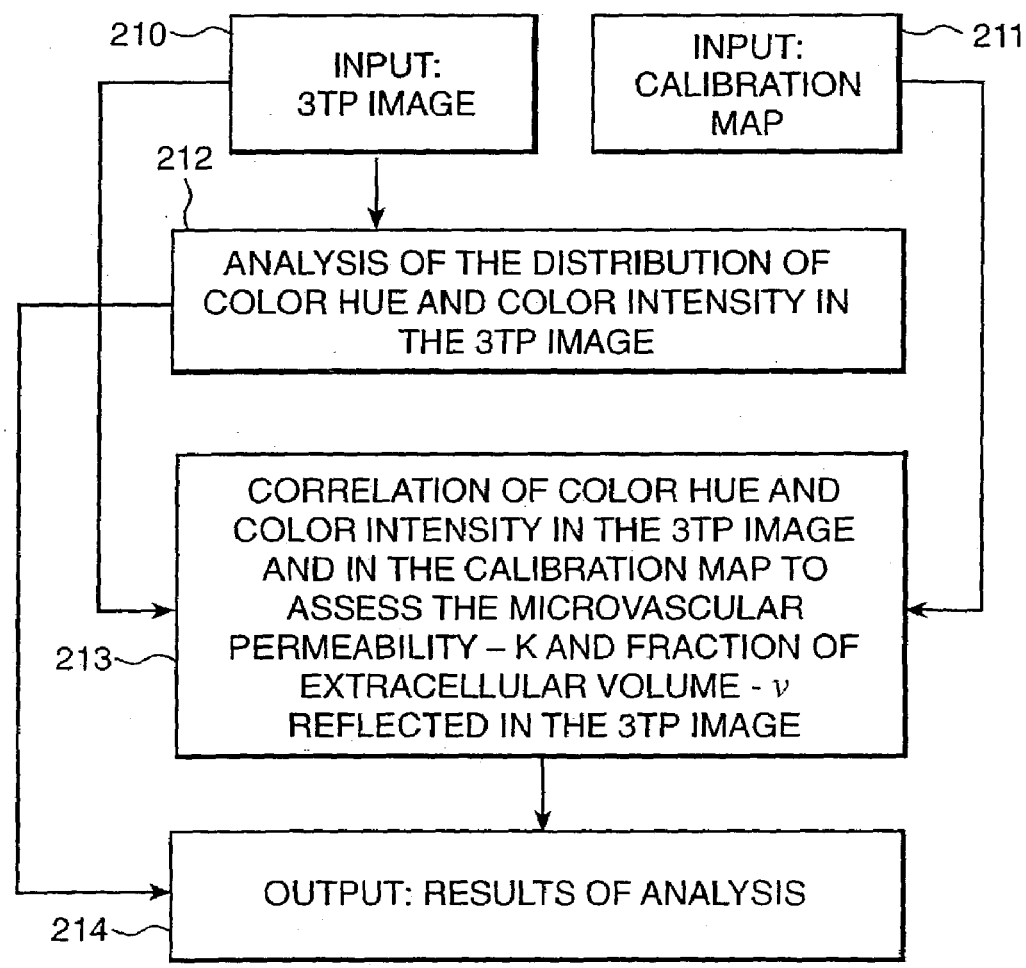
FIG. 12 is a block diagram of the apparatus of FIG. 1 showing the details of the analysis means used for MRI for analyzing 3TP images.

A specific example of that portion of the apparatus including the means for analysis of the 3TP image obtained in a tracer modulated MRI is shown in the block diagram of FIG. 12. The input in block 210 is the 3TP image. The analysis in block 212 of the 3TP image consists of analyzing color distribution and color intensity distribution, such as determining how many pixels are colored red with a certain intensity and making a similar determination for the other colors. Also, a separate analysis of intensity distribution and of color distribution can be performed. The part of the apparatus in block 211 provides means for inputting the calibration map obtained by the selecting means as shown for tracer modulated NM in FIG. 5. This calibration map is for the same t0, t1, t2 and other shared parameters as the 3TP image. Analysis of the 3TP image in terms of the two variables of the calibration map K and v is shown in block 213 of FIG. 12. This correlates color hue/color intensity in each pixel of the 3TP image to the values of the pathophysiological parameters K-microvascular permeability and v-fraction of extracellular volume determined by the color hue/color intensity in the-calibration map. Thus, the analysis is performed in terms of distributions of the two pathophysiological variables in the area or volume imaged. Finally, the apparatus in block 214 stores in a store or outputs as digital signals or displays in a display device like a monitor or is fed to a printer and a color print is obtained one or a plurality of 3TP images/and the corresponding correlated calibration maps.

Another specific example relates to control and monitoring apparatus for an irrigation system. One of the most frequently used modern techniques to irrigate or water large areas in an efficient way is by drip irrigators.

In the planning of such a system there are parameters such as the dimensions of the pipes, the extent and size of dripping holes and the pressure and timing of irrigation that can be adjusted according to the needs. These parameters will overall determine the rate of water dripping per unit area assigned here by the letter K. However, another parameter which will determine the efficiency of the irrigation is the water apparent diffusion constant in the ground, assigned here by the letter v. This diffusion rate or constant depends on the physical and chemical properties of the soil in the ground that the water passes through. Namely, in regions with light soil, such as sand, the apparent diffusion constant will be high while in regions with heavy soil it will be slow. Thus, the diffusion rate varies over the field needed to be irrigated. By the apparatus of the present invention it is possible to estimate K and v and then optimize the irrigation efficiency.

As a preliminary matter one needs to measure the amount of water per unit weight of soil. There are several ways to determine water content. One for example is: weigh accurately an amount of soil just after digging it. Dry the soil completely and then measure again the weight. The loss in weight is equivalent to the amount of water in this sample.

The samples can be taken with a spatial resolution that varies depending on the size of the field and on the accuracy needed to be reached. For example, for a very large field of tens or hundreds of square kms, it is reasonable to divide the field into 1 km' units. Thus each pixel in the final image of irrigation constructed by the novel apparatus of the present invention and in particular by the processing means will reflect behavior per 1 km². A sample of soil should be taken from the middle or any other defined location in this unit area of 1 km². The size of the sample can vary but can be small of about 1 gram. The depth from which the sample should be taken can vary according to the needs. For example, if the growth of the plants to be irrigated depends on the amount of water at the level of the roots, then the sample should be taken from this level. It is also possible to use the apparatus in 3D and take samples from the same area but at varying depth. Samples should be taken from approximately the same place (the size of the sample is much smaller than the overall unit area).

The apparatus of the invention performs as follows. The area to be tested has the dripping system ready for test and the positions of sampling are assigned. At a time, just before the start of the operation of the irrigation system, samples are taken from all the assigned positions. Then, at time point t0 the operation of the irrigation system is initiated for a pre-set time which ends before time point t1 which is determined by the calibration map. After the irrigation is stopped, a second sample is taken for measurement from each assigned position at time point t1. Finally, at the pre-set time point t2 a third sample from each assigned position is taken for measurement. The amount of water is then determined in the samples. For each position the water content in the three samples taken at time point t0, and at time points t1 and t2 will change according to a wash-in rate and wash-out pattern and will be characterized by the color hue/color intensity code as developed according to the novel apparatus and method of the present invention. The wash-in and wash-out behaviors depend on K=rate of water dripping per unit area and on v=water apparent diffusion constant in the ground. For the same v the initial rate will increase with K, for the same K the initial rate will increase with v. The wash-out pattern will also depend on K and v. If v is faster than K the fast wash-out pattern (assigned blue) will predominate. If K and v are of the same order, the green color, coding moderate wash-out, will predominate. If Q is lower than K a slow wash-out pattern, red will predominate.

The distribution of K, v over all positions (each position is described by a pixel) is determined by correlating the coloring and color intensity of the pixels (each with the color hue and color intensity) in reference to the calibration map.

The calibration map is providing wash-in intensity function and wash-out pattern in a K-v plane for t0, t1, t2 as follows: a calculation for each pair of K, v of the amount of water accumulated at time points t1 and t2 is performed based on a model known to those skilled in the art. The range of K is chosen from 0 to the maximum level of the subject irrigation system while the range of v is from 0 to the diffusion constant of pure water or, when known, the highest water diffusion constant in the field to be irrigated. To obtain optimal resolution within the range of K and v, time points t0, t1 and t2 are chosen in such a way that the K-v plane will be divided between the three wash-out patterns/colors to approximately three equal areas.

Once measurements have been made and the novel apparatus of the invention has performed its initial function, the apparatus can be adjusted to vary K (K can be varied since it depends on the irrigation system) in such a way that the irrigation in each defined area represented by a pixel will be the most efficient. For example, the moderate wash-out pattern (green) may be preferred in order to provide a constant amount of water over a defined time period. By increasing K it is possible to move from the blue region to the green for the same v. To assure the achievement of the final adjustment, it is possible to change K and then run the apparatus for the same three time points and positions in the subject field.

Another use of the color/color intensity coded map of irrigation is the preparation of a plan of planting by adjusting the kind of plants or the density of planting to the quality of irrigation dictated by the kind of soil and the irrigation system.

The new apparatus of the present invention can be utilized to test and modify the air condition planning, either for heating or for cooling or both. Described now in detail is novel apparatus for controlling and/or monitoring a heating process.

For an air condition system (heating, cooling or both) built for a whole structure having within rooms or defined spaces, such as a house, a factory, an office building, shopping mall or a complex of houses, it is important to design the system in such a way that each defined space will be conditioned efficiently and then, to verify the reality. Certain regions may be overheated while others can be over cold. The adjustment by the novel apparatus for such a structure can be done by modifying the amount of heat per unit area and unit time assigned, in this example, with the letter K. The other variable that will determine the heating capacity is the, rate of heat transfer per unit area to the surrounding environment due to imperfection in the isolation, in this example assigned the letter v.

The assessment of the heat is performed by measuring the temperature by thermocouples or thermometers placed at any number of locations within each room or defined space. Each thermometer position will define a pixel position in a 2D or 3D plan of the subject system (structure).

At a time point prior to t0, with the system turned off, readings of all temperature measuring devices in all positions are taken, determining temperature T0. Then at time point t0 the air condition system is turned on for a pre-set time, the end of which is before and close to time point t1. At time point t1, after the system has been turned off, second readings of all devices are taken determining temperatures T1. Then, after a second preset time ending at time point t2 third readings are taken determining in each position temperature T2. The temperature changes between time points t0, t1 and t2, namely, the difference between temperatures T0, T1 and T2, for each position of measurement, will depend on the amount of conditioning per unit area per time (K) released in the room and on the amount of heat lost or gained from the outside through the walls by diffusion (v). The later parameter v can be negative or positive depending on the direction of flow of heat between the environment and the position where measurement occurs. These changes can be described by a wash-in pattern of air flow and wash-out pattern of air flow. The pattern of wash-out is described by a color hue. If the temperature T1 at time t1 is higher than the temperature T2 at time t2 the washout process is defined to be fast and is assigned blue. If T1 is smaller than T2 the wash out process is defined as slow and is assigned red. If the temperature will remain the same T1=T2 (within a range predetermined by the apparatus) the wash-out process is defined to be moderate and is assigned the green color. The brightness of the colors will depend on the initial rate defined by $$\frac{(T1-T0)}{T0(t1-t0)}$$

(usually but not necessarily t0=0).

The initial rate will also depend on K and on v. For the same v, the initial rate will increase with K. For the same K the initial rate will decrease with increasing v and will increase with decreasing v also to negative values. If the place is not well isolated and the surrounding is colder, then v will be high and the change in temperature will follow the pattern of fast wash-out. If the isolation is good (v is small and close to 0), the change in temperature will follow the pattern of moderate wash-out. If the surrounding is warmer and the room is not well isolated v will have a high negative value and the change in temperature will follow the slow wash-out pattern. Using the novel color hue/color intensity concept of the present invention it will be possible to identify places that are not well conditioned, e.g. heated, and are not well isolated and places that are over conditioned, e.g. overheated.

If the air conditioning is heating, the temperature is determined by the amount of heat reaching the place where the temperature measuring device or element, e.g. thermometer, is placed and by the amount of heat that leaves this place as a result of heat loss to or heat gain from the surroundings. In certain cases defined by the size of the room and the distribution of the heat source we can assume that during the heating time the heat flow is relatively fast and equilibration in the room is rapidly achieved. Thus, the temperature will depend on the total amount of heat produced during the heating time period. K will therefore range between 0 and the maximum capacity of the heating system. The flow from or to the surroundings is determined by the same insulation, namely the same v but with opposite signs. Thus v will range between −v to +v with the actual value determined for example by the value with no insulation.

The time points t0, t1 and t2 are chosen by using a calibration map constructed based on an equation known to those skilled in the art that relates the change in temperature with time to K as described above. Although, the particular example discussed related to heating, the novel apparatus can be used with the same program and means to evaluate cooling using absolute values for the changes in temperature that determine wash-out patterns and wash-in initial rates.

The apparatus of the present invention includes a computer system operating electronically, optically or both having a memory, a central processing unit, a display, an input device for generating device event signals and coacting therewith software for use with the computer. The software (in binary or related form) comprises a computer usable medium having computer readable program code thereon including the program logic for implementing the various flow charts and block diagrams described above. Since the details of computers are well known in the art and because persons skilled in the art have sufficient expertise and knowledge to be capable of implementing the flow charts and block diagrams, a detailed description of the specific hardware has been omitted as superfluous and unnecessary to a full and complete understanding and appreciation of the present invention as described above. Those skilled in the art will be able to make and use the apparatus and method of the present invention from the detailed description and teachings contained herein.

Summarizing the 3TP method with respect to contrast enhance MRI, for a given breast lesion, changes in MRI signal intensity (SI) reflect changes in the concentration of the contrast agent. The concentration, in turn, is predominantly determined by two pathophysiological parameters that characterize malignant tumors and differentiate them from benign ones. These parameters are: the product: (blood vessel surface area)×(permeability) per unit volume; and the extracellular volume fraction (EVF) accessible to the contrast agent. From the breast MRI images, the 3TP algorithm detects the SI at each location, pixel-by-pixel, for one pre-contrast time point and two post-contrast time points (hence the name Three Time Point, or 3TP). The algorithm then codes the SI changes between the three time points using color intensity and color hue as follows:

(1) Color Intensity codes the rate at which the SI changes between the first and second time points with a resolution of 256 intensities where dark colors signify slow change and bright colors signify rapid change.

(2) Color Hue is a measure of contrast washout and is coded depending on the SI change between images recorded at the second and third time points. The color coded 3TP images are related to pathophysiology via the mathematical model described above so that color hue and intensity are related to the product, (vessel surface area×permeability), and to the extravascular space (EVF), respectively, yielding a "calibration map", used for interpretation. Cancers typically show more bright red regions, reflecting the presence of increased vessel permeability and higher cell density. Benign tumors and normal breast conditions typically demonstrate greater areas of blue, indicative of the presence of lower cell density and thus higher extracellular volume with diminished vascular permeability.

FIG. 17 shows in view (a) that MLO mammographic projection of a 49 yo woman does not show 15 mm cancer which was palpable and diagnosed by in-office FNA as infiltrating ductal cancer; in view (b) that subtraction sagital MRI (0 minute (pre-contrast) image subtracted from 2 minute image shows ring-enhancing, spiculated malignancy in the anterior breast (arrow), and posteriorly, a small intramammary lymph note also enhances, but has a characteristic morphology, including fatty hilus (arrowhead); in view (c) that 3TP parametric similar to that of 1b, but with overlay of colored pixels superimposed on MRI image by 3TP software based on a physiological model (described in text) reveals bright red indication of high probability for malignancy and this lesion was prospectively given a score of 5 (highly suspicious for malignancy); and in view (d) shows a calibration map corresponding to the patient shown in 1a. The calibration map shows color hue (red, green, blue) based on differences in signal intensity between the second and third images of the three image 3TP image set. Color intensity is based on the difference in SI between the first and second images of the image set. As described in the text, areas of high vessel permeability×surface area and low extravascular volume fraction (EVF), typical of malignancy, are coded as bright red. For optimal discrimination of benign and malignant lesions, the imaging parameters are chosen to approximately divide the calibration map into equal areas of red, green and blue.

Accuracy of diagnosis relies on judicious selection of the three time points. This selection is made by adjusting time points so that, given the imaging parameters, the red, green and blue pixels are equally distributed in this map. For the imaging parameters we employed, we found that the two post contrast imaging points that provided this optimal "calibration map" occurred at two and six minutes after contrast injection. Attempting interpretation using other time points will shift the distribution of red, green and blue pixels toward a higher sensitivity or specificity. By seeking those points in which red, green and blue pixels were equally distributed throughout the calibration map, it is hypothesized that the most accurate diagnosis could be obtained. The color convention used, is that cancer is now associated with red pixels, and benign conditions with blue pixels, contrary to any earlier convention.

MR Imaging

For a specific example of clinical testing, imaging was performed at 1.5 Tesla (GE Medical Systems, Waukesha, Wis.) using a phased array breast coil (MRI Devices, Waukesha, Wis.). A three dimensional gradient echo acquisition was employed using parameters: TR=15 msec; TE=4.2 msec; flip angle=30 degrees FOV=16–18 cm; matrix=256×256; NEX=1.0, and slice thickness=2.2–3.0 mm. Seven consecutive image sets of 56 slices (interpolated from 28 slices), were obtained over 14 minutes and 45 seconds.

Gadodiamide (Omniscan—Nycomed Laboratories. Princeton, N.J.) was injected three minutes after the beginning of the scan series, i.e. 1 minute after the start of the second scan sequence. Contrast was administered at 2 cc/sec, followed by 15 cc of saline flush, also delivered at 2 cc/sec, using an automated pump (Medrad Corporation, Indiancis, Pa.).

Image Interpretation and Data Analysis

Figure 18A:
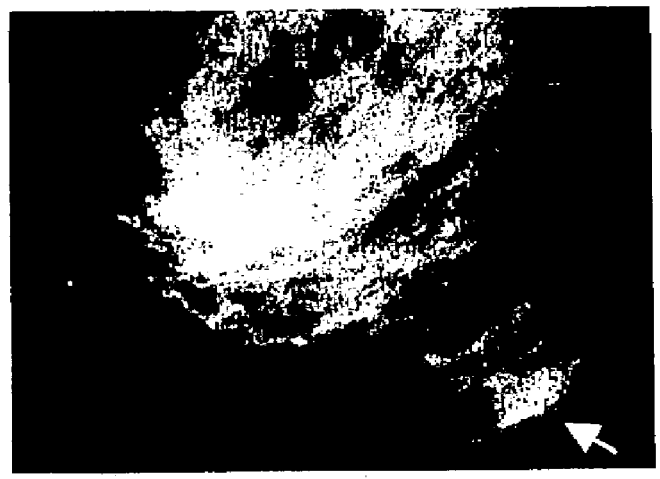
FIGS. 18(a) and (b) show, respectively,
 (a) MLO mammographic projection showing an ovoid focal lesion along the inferior mid breast (arrow) in a 69 yo woman. Pathological diagnosis, via excisional biopsy, was benign breast tissue.
 (b) 3TP sagital MRI parametric image shows virtually all dark blue pixels indicating a lesion with low values of vessel permeability×surface area and extravascular space—indicators of benignity. The prospective 3TP diagnosis was benign (suspicion level 2)
Figure 18B:

For the specific example of clinical testing, MR images were sent by File Transfer Protocol (ftp) from the laboratory performing clinical trials to the research laboratory for analysis. Interpretation of images involved visually examining each of the slices computed from imaging time points at 0, 2 and 6 minutes for a coherent group of pixels which could indicate a lesion. Prior experience with the 3TP method has shown that when a lesion has >15% red pixels, it is likely malignant; if few red pixels (<10%) are present, the lesion is likely benign. Benign lesions typically show a high fraction of blue pixels (>50%) and low color intensity. In this regard, note FIG. 18 which shows in view (a), a MLO mammographic projection showing an ovoid focal lesion along the inferior mid breast (arrow) in a 69 yo woman; pathological diagnosis, via excisional biopsy, was benign breast tissue; and in view (b) a 3TP sagital MRI parametric image showing virtually all dark blue pixels indicating a lesion with low values of vessel permeability×surface area and extravascular space–indicators of benignity; the prospective 3TP diagnosis was benign (suspicion level 2).

For many lesions, diagnosis, simply based on these criteria, is conclusive. For visually indeterminate cases, a parametric 3TP image can be computed using the additional data points, 4 and 8 minutes, available as part of a seven image set. This technique shifts the calibration map towards one in which sensitivity is increased, at the price of specificity, with the idea that misdiagnosing a malignancy as benign is worse than misdiagnosing a benign lesion as malignant. With the three new time points, if the green pixels become red, the lesion can be diagnosed as malignant.

Figure 19A:
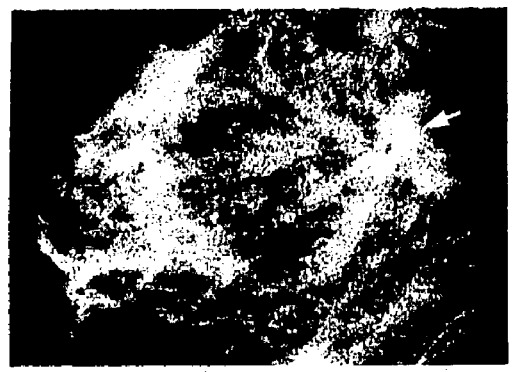
FIGS. 19(a), (b) and (c) show, respectively,
 (a) MLO mammographic projection showing an area of ill-defined density and architectural distortion (arrow) in a 64 yo woman. Diagnosis, via excisional biopsy, was infiltrating ductal cancer.
 (b) Subtraction MRI (image at 0 minutes (pre-Gd contrast) subtracted from image at time 6 minutes) showing an irregular area of enhancement corresponding to the mammographic lesion.
 (c) Top three images are magnified views from adjacent slices of the central portion of the 3TP parametric image, calculated using 0, 2 and 6 minute MR images. The results show a visually indeterminate number of red pixels. The bottom three images are these same image locations, but 3TP images were recalculated using 0, 4 and 8 minute MR images. There is a shift toward an increasing number of red pixels, indicating malignancy to be more probable than benignancy. The prospective 3TP diagnosis was malignant, at suspicion level 4.
Figure 19B:
Figure 19C:
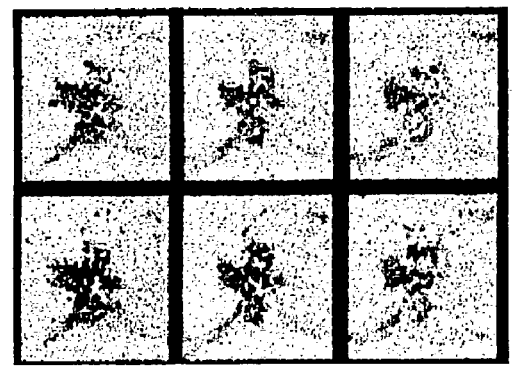

FIG. 19 shows in view (a) a MLO mammographic projection showing an area of ill-defined density and architectural distortion (arrow) in a 64 yo woman; diagnosis, via excisional biopsy, was infiltrating ductal cancer; in view (b) subtraction MRI (image at 0 minutes (pre-Gd contrast) subtracted from image at time 6 minutes) showing an irregular area of enhancement corresponding to the mammographic lesion; and in view (c) top three images being magnified views from adjacent slices of the central portion of the 3TP parametric image, calculated using 0, 2 and 6 minute MR images. The results show a visually indeterminate number of red pixels. The bottom three images are these same image locations, but 3TP images recalculated using 0, 4 and 8 minute MR images. There is a shift toward an increasing number of red pixels, indicating malignancy to be more probable than benignancy. The prospective 3TP diagnosis was malignant, at suspicion level 4.

The final diagnosis was graded using a scale slightly modified from the BIRAD scale used for mammographic interpretation in the United States:

1 = very likely to be benign
2 = probably benign
3 = indeterminate (6 month f/u)
4 = possibly malignant (biopsy)
5 = very likely to be malignant (biopsy)

Figure 20:
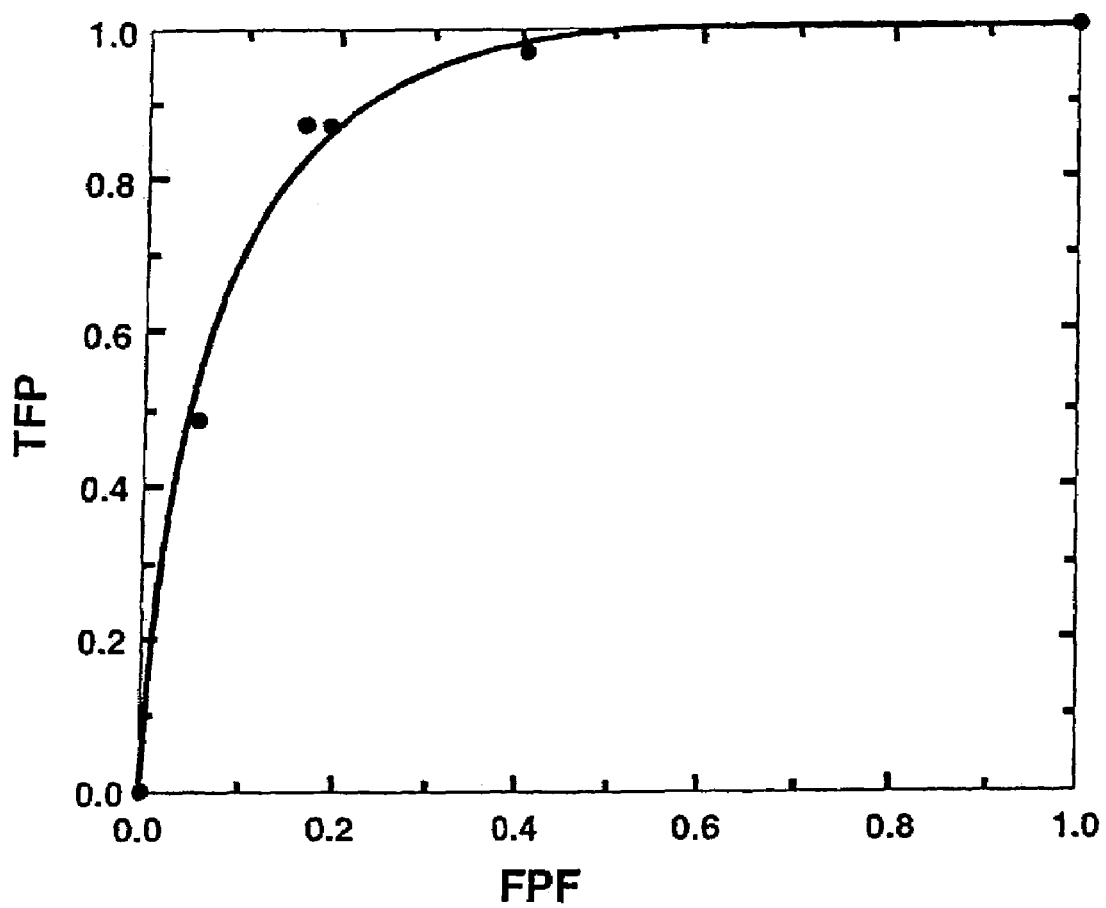
FIG. 20 shows a ROC curve derived from 3TP data in which lesion location was supplied to the researcher, but no other clinical information was supplied. The researcher was then asked to supply a number from 1 to 5 indicating probability for malignancy or benignity.

In the clinical test noted above, the 3TP method correctly diagnosed 27 of 31 malignant (grade 4 or 5) and 31 of 37 benign lesions (grade 1, 2 or 3). The ROC curve, based on the BIRAD-like classifications scheme is shown in FIG. 20. The ROC curve of FIG. 20 was derived from 3TP data in which lesion location was supplied to the researcher, but no other clinical information was supplied. The researcher was then asked to supply a number from 1 to 5 indicating probability for malignancy or benignity. The area under the ROC curve, $A_z$, was 0.911 and the standard deviation in $A_z$ was 0.036. Only one lesion was graded as indeterminate (grade 3)—pathology showed a benign intraductal papilloma. The results, classified by mammographic lesion, were further categorized as follows:

| Lesion Type | Sensitivity | Specificity |
| --- | --- | --- |
| All 68 lesions | 87% | 84% |
| 45 solid masses | 96% | 82% |
| Microcalcifications | 63% | 81% |

Figure 21A:
FIGS. 21(a), (b) and (c) show, respectively,
 (a) Optical close-up of mammographic magnification CC view—66 yo woman with cluster of microcalcifications in the superior mid breast. Pathological diagnosis was DCIS, low to intermediate grade.
 (b) Optical close-up of subtraction sagital MRI image—6 minutes after injection of Gadodiamide. Small irregular focus of enhancement (arrow) corresponds to cluster of microcalcifications.
 (c) Optical close-up of sagital 3TP image shows an area of predominantly bright green pixels thought to be benign (score=2). A total of three out of eight DCIS lesions were misdiagnosed as benign by the 3TP method. An area of future investigation is to determine whether there is a specific pattern for DCIS that will allow increased accuracy of diagnosis.
Figure 21B:
Figure 21C:

There were four false negative results: three lesions showing microcalcifications without mass and one small solid lesion. The three foci of microcalcifications were all pathologically diagnosed as ductal cancer in situ (DCIS)—two intermediate grade (8 and 14 mm); and one low grade (four ducts). One example of a false negative result is shown in FIG. 21 which shows in view (a) an optical close-up of mammographic magnification CC view —66 yo woman with cluster of microcalcifications in the superior mid breast; pathological diagnosis was DCIS, low to intermediate grade. In view (b) of FIG. 21 is shown an optical close-up of subtraction sagital MRI image—6 minutes after injection of Gadodiamide; small irregular focus of enhancement (arrow) corresponds to cluster of microcalcifications. FIG. 21 view (c) shows an optical close-up of sagital 3TP image showing an area of predominantly bright green pixels thought to be benign (score=2). A total of three out of eight DCIS lesions were misdiagnosed as benign by the 3TP method. An area of future investigation is to determine whether there is a specific pattern for DCIS that will allow increased accuracy of diagnosis. Note that five other foci of DCIS were correctly diagnosed as malignant. The misdiagnosed solid lesion measured 5 mm in diameter and had a pathological diagnosis of invasive ductal cancer. In the same breast, two larger lesions, measuring 8 and 14 mm were correctly diagnosed as malignant.

Figure 22A:
FIGS. 22(a), (b) and (c) show, respectively,
 (a) Ultrasound examination of a mammographically occult palpable lesion in a 45 yo woman showing a gently lobulated mass, without acoustic shadowing, typically of fibroadenoma, which was confirmed by ultrasound-guided FNA.
 (b) Subtraction MIP MRI, 6 minutes after Gadodiamide injection, shows that the fibroadenoma confirmed by ultrasound is the largest of multiple enhancing smaller lesions. At the workstation, many of these smaller lesions showed an enhancement profile similar to that of the larger, palpable and sonographically confirmed lesion. In clinical practice evaluation of the multiple other enhancing lesions by manual placement of an ROI is impractical. Though internal septations are said to be an important MRI sign of fibroadenoma, they were not noted in this patient.
Figure 22B:
Figure 22C:

Six false positive results were obtained: one 11 mm focus of fibrocystic change; one 3 mm focus of schlerosing adenosis; one 9 mm intraductal papilloma; one 10 mm focus of mixed pathology (fibrocystic change and fibroadenoma); one 3 mm intraductal papilloma and one 9 mm fibroadenoma. Of fourteen fibroadenomas, 12 were correctly diagnosed as benign, while two were thought to be a malignancies. FIG. 22 shows in view (a) ultrasound examination of a mammographically occult palpable lesion in a 45 yo woman showing a gently lobulated mass, without acoustic shadowing, typically of fibroadenoma, which was confirmed by ultrasound-guided FNA. In FIG. 22 view (b) subtraction MIP MRI, 6 minutes after Gadodiamide injection, shows that the fibroadenoma confirmed by ultrasound is the largest of multiple enhancing smaller lesions. At the workstation, many of these smaller lesions showed an enhancement profile similar to that of the larger, palpable and sonographically confirmed lesion. In clinical practice evaluation of the multiple other enhancing lesions by manual placement of an ROI is impractical. Though internal septations are said to be an important MRI sign of fibroadenoma, they were not noted in this patient. In FIG. 22 view (c) 3TP parametric image showed predominantly central bright green and peripheral blue pixels, consistent with a benign lesion (score=2). The 3TP parametric image showed no other suspicious lesions.

Figure 23B:
Figure 23C:

There were 7 patients (12.5%) who inadvertently benefited from having breast MRI. In four patients, a second or even third focus of malignancy was detected that was unexpected by mammography and changed the surgical approach. An example is shown in FIG. 23 in which view (a) of an optical close-up of mammography (MLO projection) in a 44 yo woman showed a spiculated mass (straight arrow). An unexpected, mammographically occult, $2^{nd}$ lesion was detected at the location indicated by the curved arrow, as a result of this patient volunteering for the 3TP clinical trial. Pathological diagnosis in both cases was infiltrating ductal cancer. As is shown in FIG. 23 view (b) a 3TP parametric sagital plane image of lesion suspected to be malignant by mammography. High predominance of bright red pixels indicates high value of the product of vascular permeability× surface area, and low extravascular volume fraction, indicating high probability of malignancy (score=5). In FIG. 23 view (c) a 3TP parametric image of a second adjacent sagital slice showed a second site very suspicious for malignancy (score 5). Both sites were biopsied confirming unsuspected multifocal malignancy.

In one patient, where the radiologist, based on mammographic results, suspected a 1 cm tumor, MRI revealed that it was actually 4 cm in size, this was subsequently diagnosed as an infiltrating ductal cancer.

In one patient, in whom a well marginated lesion with rapid contrast washout was seen, the surgeon declined imaging guidance in removal of the palpable lesion. However, when the pathological report described only benign breast tissue, the surgeon, based on the MRI data, was urged to repeat the ultrasound, which confirmed lack of excision. Image-guided excision was then performed, now showing a benign papilloma. Finally, in one patient, after a failed mammographically-guided localization of mammographically vague and sonographically occult lesion, MRI-guided needle localization was used to excise the lesion and arrive at the diagnosis—invasive ductal cancer.

For 68 pathologically proven lesions, the 3TP method, in a heterogeneous population, achieved an overall sensitivity of 87% and a specificity of 84% for detection of malignancy. Of note is that when results from the 45 solid masses were reviewed, the 3TP method achieved a sensitivity and specificity of 96% and 82%, respectively. Only one 5 mm malignancy was misdiagnosed as benign in a patient in whom two other larger malignant (8 and 14 mm) and one benign lesion (29 mm post lumpectomy seroma) were correctly diagnosed.

Although the invention has been described in detail, nevertheless changes and modifications which do not depart from the teachings of the present invention will be evident to those skilled in art. Such changes and modification are deemed to come within the purview of the present invention and the appended claims.

The invention claimed is:

1. Apparatus for monitoring a system in which a fluid flows and which is characterized by a change in the system with time in space comprising: (a) a monitor for monitoring a preselected place in the system for collecting data indicative of a system parameter that varies with time as a function of at least one variable related to system wash-in and wash-out behavior; (b) first data processor responsive to the monitor for receiving the collected data and processing same; (c) a selector for controlling the monitor for setting parameters of data collection, and for receiving inputs of system parameters including said system parameter and a plurality of time points correlated to a system event; (d) a second data processor including: (1) a first divider for dividing the space defined by at least two variables, each ranging from a minimum to a maximum, into a grid; (2) first determiner for determining for each grid location a calculated value and intensity function indicative of the wash-in of the parameter being monitored for each time point; (3) first normalizer for determining a grid location of maximum intensity and normalizing all grid locations with reference to the maximum; (4) first colorizor for coloring all grid locations one of a plurality of colors based on a color function indicative of wash-out behavior; (5) an arranger for arranging all grid locations for all time points into a composite to develop a calibration map of the grid with each grid location correlated to a color hue/color intensity; (6) an analyzer for analyzing the calibration map to determine if the attributes of the calibration map meet a preselected standard, if not, to implement the plurality of time points or a system parameter and iterate until the resultant calibration map meets said standard; (e) said first data processor receiving as further inputs the plurality of time points and the maximum of the intensity function as determined in the second data processor and further including: (1) a second divider for spatially dividing the preselected place in the system into spatial units; (2) a second determiner for determining for each spatial unit a value and intensity function indicative of wash-in behavior based on the collected data for each time point; (3) a second normalizer for normalizing the intensity of each spatial unit based on maximum intensity obtained from the first normalizing means; (4) a second colorizor for coloring all spatial units one of a plurality of colors based on the color function indicative of wash-out behavior of said first colorizing means; (5) a second arranger for arranging all spatial units for all time points into a composite of the preselected space with each spatial unit correlated to a color hue/color intensity.

2. Apparatus according to claim 1 wherein the first colorizor provides one color if the color function is greater than or equal to X indicative of slow wash-out behavior, a second color if the color function is less than X and greater than or equal to Y indicative of moderate wash-out behavior, and a third color if the color function is less than Y indicative of fast wash-out behavior, where X and Y are decimals less than one with X being positive and Y being negative.

3. Apparatus according to claim 2 wherein X equals 0.1 and Y equals −0.1.

4. Apparatus according to claim 1 wherein three time points are used t0, t1 and t2, with t0 being the time at the beginning of the system event, t1 being a time after t0 and t2-being a time after t1.

5. Apparatus according to claim 1 wherein the system event is the injection of a tracer material into the fluid flowing in the system.

6. Apparatus according to claim 5 wherein the apparatus is an MRI system.

7. Apparatus according to claim 1 wherein a display is provided to display the resultant calibration map and the composite of the preselected place.

8. Apparatus according to claim 1 wherein a storage is provided to store the resultant calibration map and the composite of the preselected place.

9. Apparatus according to claim 1 wherein a printer is provided to print the resultant calibration map and the composite of the preselected place.

10. Apparatus for monitoring a system in which a fluid flows and which is characterized by a change in the system with time in space comprising: (a) a monitor including a first output for monitoring a preselected place in the system for collecting data indicative of a system parameter that varies with time as a function of at least two variables related to wash-in and wash-out behavior, (b) a first processor including a second output and a first input for receiving the collected data from the first output and processing same, (c) a selector including a third output for controlling the monitor, for setting parameters of data collection and for providing input to the first input, the selector including: (i) an input receiver for receiving inputs of system parameters including said system parameter and a plurality of preselected time points correlated to a system event, (ii) a second processor including: (1) a first divider for dividing the space defined by the at least two variables, each ranging from a minimum to a maximum, into a grid, (2) a first determiner for determining for each grid location a calculated value of intensity of the parameter being monitored for each time point, (3) a first normalizer for determining the maximum intensity of the grid locations and normalizing all grid locations with reference to the maximum, (4) a first colorizor for coloring all grid locations one of a plurality of colors based on a correlation with wash-out behavior, (5) an arranger for arranging all grid locations for all time points into a composite to develop a calibration map of the grid with each grid location correlated to a color hue/color intensity, (6) an analyzer for analyzing the calibration map to determine if the color distribution of the calibration map satisfies a predetermined condition and, if not, to implement one of the plurality of time points and a system parameter and inputting to the input receiver for iteration until the resultant calibration map satisfies the predetermined condition, (d) said first processor receiving as further inputs the plurality of time points and the maximum of the intensity function as determined in the second processor, and further including: (i) a second divider for spatially dividing the preselected place in the system into spatial units, (ii) a second determiner for determining for each spatial unit a value and intensity based on the collected data for each time point, (iii) a second normalizer for normalizing the intensity of each spatial unit based on maximum intensity obtained from the first normalizer, (iv) a second colorizor for coloring all spatial units one of a plurality of colors based on the correlation with wash-out behavior used in the first colorizor, (v) a second arranger for arranging all spatial units for all time points into a composite of the preselected place with each spatial unit correlated to a color hue/color intensity.

11. Data processing system for producing a calibration map for use with a monitored system in which a fluid flows and which is characterized by a change in the monitored system with time in space and wherein the monitoring occurs at a preselected location comprising: (a) computer processor for processing data; (b) storage means for storing data on a storage medium; (c) means for initializing the storage medium; (d) a first processor controller for dividing the space defined by two variables, each ranging from a minimum to a maximum, into a grid, said variables being correlated to a preselected parameter of the monitored system; (e) a second processor controller for determining for each grid location a calculated value and intensity function of the parameter at each of a plurality of time points; (f) a third processor controller for determining the maximum of the intensity function of the grid locations and normalizing all grid locations with reference to the maximum; (g) a fourth processor controller for coloring all grid locations one of a plurality of colors based on a color function correlated with monitored system behavior; (h) a fifth processor controller for arranging all grid locations for all time points into a composite to develop a calibration map of the grid with each grid location correlated to a color hue/color intensity; and (i) a sixth processor controller for analyzing the calibration map to determine if the attributes of the calibration map meet a predetermined condition, and, if not, to implement the plurality of time points or variables and iterating until the attributes of the resultant calibration map meet the predetermined condition.

12. The data processing system of claim 11 wherein the attribute is color distribution.

13. The data processing system of claim 12 wherein the condition is substantially equal coloring of the colors of the calibration map.

* * * * *